United States Patent
Takizawa et al.

(10) Patent No.: US 8,594,767 B2
(45) Date of Patent: Nov. 26, 2013

(54) MAGNETIC RESONANCE IMAGING APPARATUS AND MAGNETIC RESONANCE IMAGING METHOD

(75) Inventors: Masahiro Takizawa, Tokyo (JP); Tetsuhiko Takahashi, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 822 days.

(21) Appl. No.: 12/523,343

(22) PCT Filed: Feb. 1, 2008

(86) PCT No.: PCT/JP2008/051660
§ 371 (c)(1),
(2), (4) Date: Jul. 16, 2009

(87) PCT Pub. No.: WO2008/096677
PCT Pub. Date: Aug. 14, 2008

(65) Prior Publication Data
US 2010/0087729 A1    Apr. 8, 2010

(30) Foreign Application Priority Data
Feb. 9, 2007 (JP) .................. 2007-030795

(51) Int. Cl.
*A61B 5/05* (2006.01)
(52) U.S. Cl.
USPC ........... 600/415; 600/410; 600/411; 600/413; 324/307; 324/309
(58) Field of Classification Search
USPC ................. 324/307; 600/410, 411, 413, 415
See application file for complete search history.

(56) References Cited

U.S. PATENT DOCUMENTS

| | | | | |
|---|---|---|---|---|
| 6,323,646 | B1 * | 11/2001 | Zhou et al. | 324/309 |
| 6,353,752 | B1 * | 3/2002 | Madore et al. | 600/410 |
| 6,587,707 | B2 * | 7/2003 | Nehrke et al. | 600/410 |
| 6,912,415 | B2 | 6/2005 | Kruger et al. | |
| 6,963,768 | B2 * | 11/2005 | Ho et al. | 600/415 |

FOREIGN PATENT DOCUMENTS

| | | |
|---|---|---|
| JP | 2004-527301 | 9/2004 |
| JP | 2005-185732 | 7/2005 |

OTHER PUBLICATIONS

Aldefeld, B., et al., "Respiratory-Gated Continuously Moving Table 3D MRI", *Proc. Intl. Soc. Mag. Reson. Med.*, vol. 14, p. 212, 2006.
Bornert, P., et al., "Multi-Contrast Continuously Moving Table 3D MRI Imaging", *Proc. Intl. Soc. Mag. Reson. Med.*, vol. 13, p. 2368, 2005.

(Continued)

*Primary Examiner* — Unsu Jung
*Assistant Examiner* — Joseph M Santos Rodriguez
(74) *Attorney, Agent, or Firm* — Cooper & Dunham LLP

(57) ABSTRACT

When multiple types of imaging are performed while moving a table on which a subject to be examined is placed, an imaging efficiency is improved and a high-quality image is obtained within a short time. Therefore, within a predetermined time interval such as an identical period of a periodic living body motion, a predetermined number of echo signals from each of the multiple types of imaging sequences are acquired and the table on which the subject to be examined is placed is moved. Along with the movement of the table, data items within the same range in the Ky-direction as to each of the imaging sequences are acquired, the moving speed of the table is controlled in such a manner that the acquired data items become continuous in the x-direction, and images are reconstructed based on the data items obtained respectively from the imaging sequences.

24 Claims, 13 Drawing Sheets

(56) References Cited

OTHER PUBLICATIONS

Bornert, P., et al., "Fast Whole-Body 3D Water/Fat Scoring", *Proc. Intl. Soc. Mag. Reson. Med.*, vol. 14, p. 2305, 2006.

Hoogeveen, R.M., "Total-body moving-bed cine phase-contrast MR angiography", *Proc. Intl. Soc. Mag. Reson. Med.*, vol. 13, p. 1710, 2005.

Kruger, David G., et al., "Continuously Moving Table Data Acquisition Method for Long FOV Contrast-Enhanced MRA and Whole-Body MRI", *Magnetic Resonance in Medicine*, vol. 47, pp. 224-231, 2002.

Japanese official action dated Mar. 5, 2013 in corresponding Japanese patent application No. 2008-557085 filed Dec. 26, 2003.

* cited by examiner

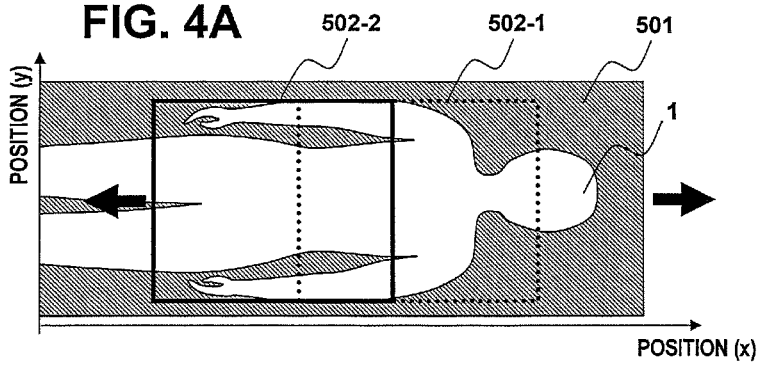
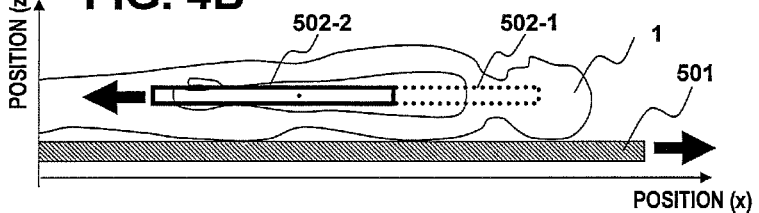
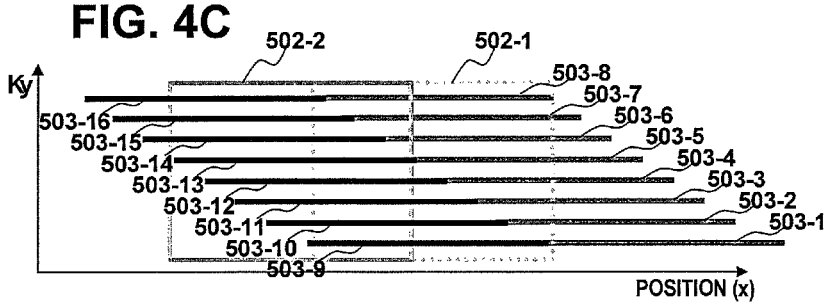
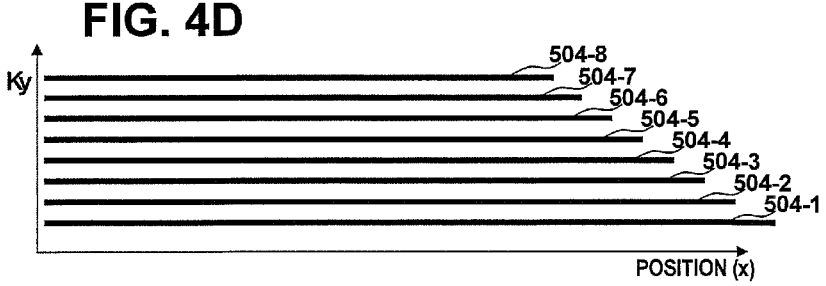

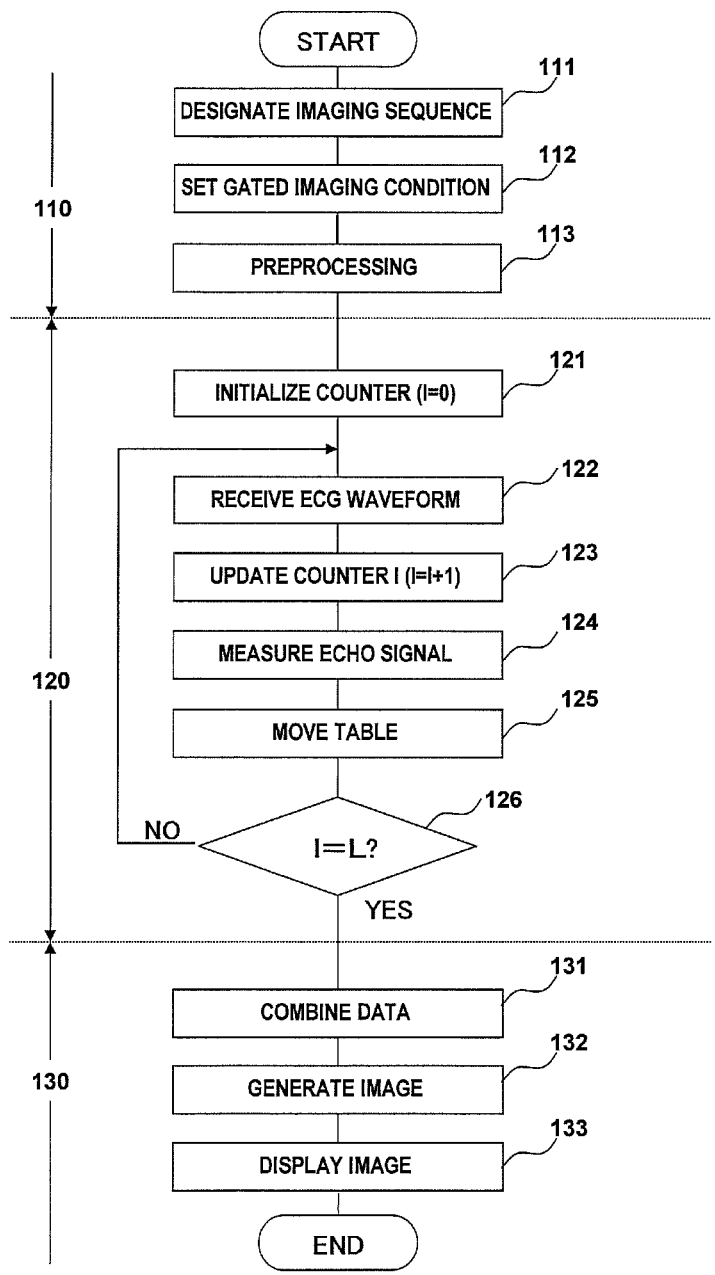

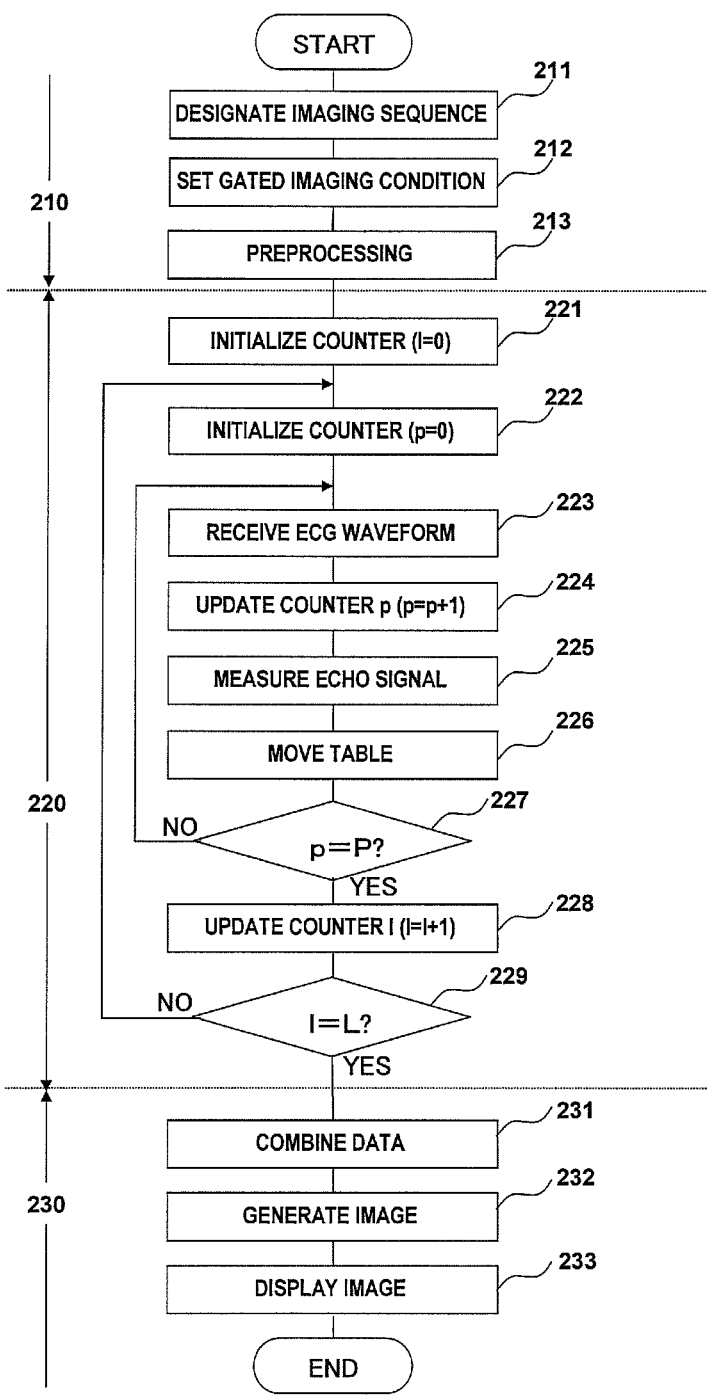

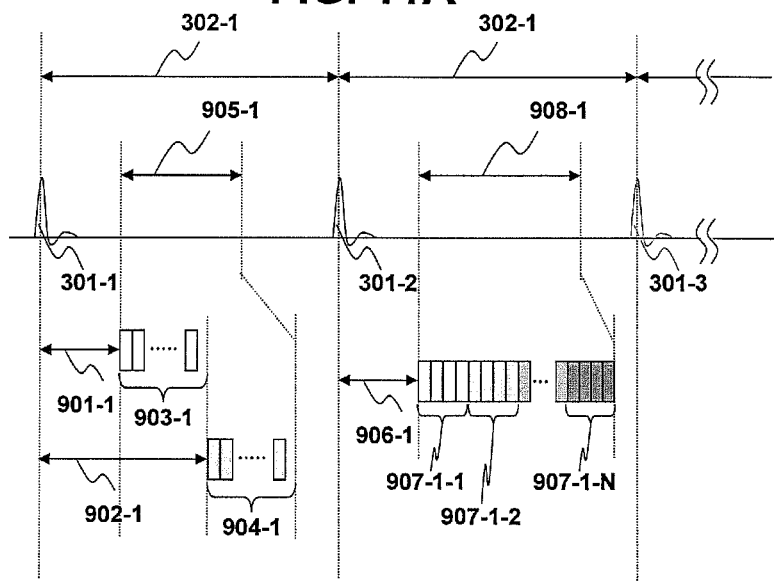
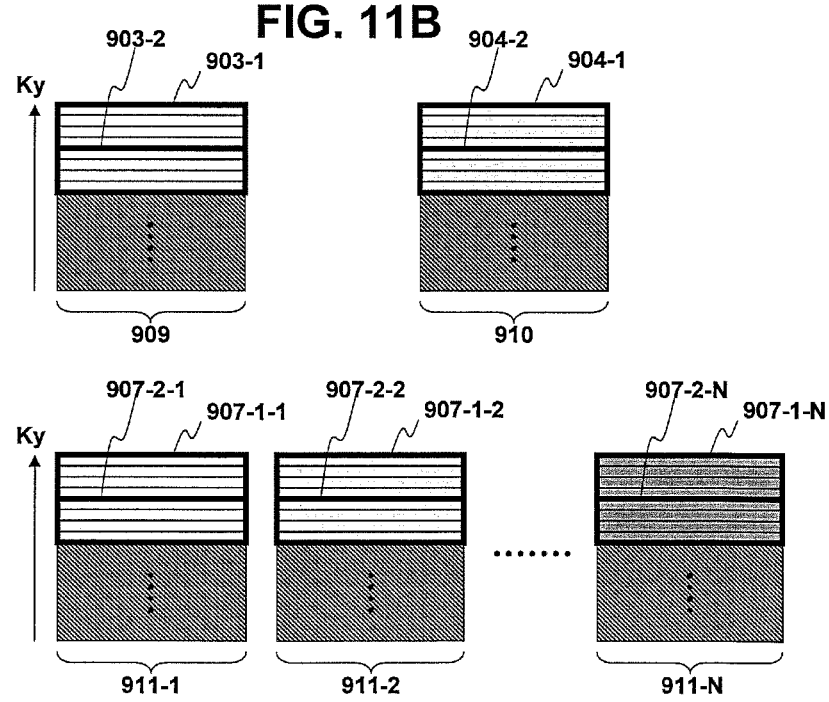

MAGNETIC RESONANCE IMAGING APPARATUS AND MAGNETIC RESONANCE IMAGING METHOD

TECHNICAL FIELD

The present invention relates to a magnetic resonance imaging (hereinafter, referred to as "MRI") apparatus which obtains a tomographic image of an area to be examined of a subject to be examined by using a nuclear magnetic resonance phenomenon, and in particular, it relates to a technique to carry out multiple types of imaging while moving a table on which the subject to be examined is placed.

BACKGROUND ART

In the MRI apparatus, an imaging sequence is repeatedly executed at predetermined time intervals, thereby acquiring a group of echo signals, which is necessary for reconstructing an image. If the subject to be examined moves while the imaging sequence is executed, discontinuity may occur between the echo signals, causing a false image, which is referred to as an artifact, when the image is reconstructed. Considering the situation above, the imaging sequence is executed, gated with a periodic motion such as respiration and heart beating among the motion of the subject to be examined, so as to eliminate the body motion apparently, thereby executing a gated imaging that reduces the artifact.

In order to respond to a request for imaging a wide range, there is a moving table imaging method which performs measurement while a table placing the subject to be examined thereon moves, so that a wide-range image of the subject to be examined is obtained (see non-patent document 1, for example). In the moving table imaging, while the imaging sequence is repeatedly executed, the table is continuously moved to update the subject to be examined position, and then the echo signals obtained at respective positions are combined to reconstruct an image.

[Non-Patent Document 1]
D. G. Kruger et.al., Continuously Moving Table Method for Extended FOV 3D MRI, Proc. Intl. Soc. Mag. Reson. Med. 10 (2002): 294.

DISCLOSURE OF THE INVENTION

Problem to be Solved by the Invention

In addition to the wide-range imaging, there is another request to perform multiple types of imaging, such as a multi-slice imaging and an acquisition of multiple images with different contrast. However, in the moving table imaging, while the table is continuously moved, imaging of different regions of the subject to be examined is repeated, in order to achieve a wide-range of imaging. When the multi-slice imaging is performed or multiple images different in contrast are acquired, it is necessary to execute imaging sequences being different respectively. Therefore, it is required to repeat the following; every time imaging of overall range is finished by a single imaging sequence, the table position is reset and another imaging is performed with the table movement. Consequently, it is cumbersome to put back the table position every single time, and also a total imaging time is prolonged.

Furthermore, if an artifact has to be reduced to obtain a high quality image, it is necessary to combine a gated imaging. In the gated imaging, a repetition time of the imaging sequence is restricted by a time phase of respiration or heart beating. Therefore, even when the imaging sequence is executed only once, a useless time such as waiting time may occur. In the case where multiple imaging sequences are executed, if each imaging sequence is performed for every single time, such useless waiting time may occur for each of the imaging sequences, and the total imaging time may be further prolonged. Therefore, if the gated imaging is combined with the moving table imaging, additional time becomes necessary such as a waiting time caused by the gated imaging and a time for resetting the table position every single time caused by the moving table imaging. Accordingly, a long time may be taken for the imaging, causing inefficiency.

The present invention has been made in view of the situation above, and an object of the invention is to improve imaging efficiency and obtain multiple types of images, when multiple types of imaging are performed while a table on which a subject to be examined is placed is moved. In particular, an object of the present invention is to improve efficiency when the imaging is combined with a periodic body motion of the subject to be examined.

Means to Solve the Problem

In the present invention, at a predetermined time interval such as during an identical period of periodic living-body motion, following processes are performed; acquisition of a certain number of echoes in each of the multiple types of imaging sequences and movement of a table on which a subject to be examined is placed thereon.

Specifically, the present invention provides a magnetic resonance imaging apparatus including, an imaging control means for executing an imaging sequence to image a desired area of a subject to be examined, a signal processing means for reconstructing an image from signals obtained from a result of executing the imaging sequence, and a table control means for controlling movement of a table on which the subject to be examined is placed, wherein, the imaging control means executes multiple imaging sequences while the table control means moves the table from a desired first position to a desired second position with the passage of time, and the signal processing means reconstructs images respectively by the multiple sequences as to an area from the first position to the second position, using the signals obtained as a result of executing each of the multiple imaging sequences.

The present invention further provides a magnetic resonance imaging method for executing multiple imaging sequences to image a desired area of a subject to be examined, while moving a table on which the subject to be examined is placed, and for reconstructing images from echo signals obtained from the multiple imaging sequences, including, an imaging step for executing the multiple imaging sequences while the table moves from a desired first position to a desired second position with the passage of time, and an image reconstruction step for reconstructing images respectively by the multiple imaging sequences as to an area from the first position to the second position, using the signals obtained as a result of executing each of the multiple imaging sequences.

Effect of the Invention

According to the present invention, if multiple types of imaging are performed while the table placing the subject to be examined thereon is moved, it is possible to obtain multiple types of images with improved imaging efficiency. In particular, in combination with a periodic body motion of the subject to be examined, the imaging efficiency can be enhanced more.

BEST MODE FOR CARRYING OUT THE INVENTION

<First Embodiment>

Hereinafter, a preferred embodiment of the present invention will be explained. Firstly, with reference to FIG. 1, an MRI apparatus according to the present embodiment will be schematically explained. FIG. 1 is a block diagram showing an overall configuration of the MRI apparatus according to the present embodiment.

The MRI apparatus according to the present embodiment is directed to acquisition of a tomographic image of a subject to be examined, by using a nuclear magnetic resonance (NMR) phenomenon. As shown in FIG. 1, the MRI apparatus is provided with a static magnetic field generation system 2, a gradient magnetic field generation system 3, a sending system 5, a receiving system 6, a signal processing system 7, a sequencer 4, a central processing unit (CPU) 8, an operating part 25, a table controller 27, and a living body signal detector 28.

The static magnetic field generation system 2 generates a homogeneous static magnetic field in a body axis direction or in a direction orthogonal to the body axis, in the space surrounding the subject to be examined 1, incorporating a magnetic field generation means, such as a permanent magnet system, a normal conducting system, or a superconducting system, being located around the subject to be examined 1.

The gradient magnetic field generation system 3 is made up of the gradient magnetic field coils 9 wound in the three axial directions X, Y, and Z, and a gradient power supply 10 that drives each of the gradient magnetic field coils, and drives the gradient power supply 10 for each of the gradient magnetic field coils, in response to a command from the sequencer 4, so as to apply gradient magnetic fields on the subject to be examined 1 in three axis direction X, Y, and Z, respectively. More specifically, a slice selective gradient magnetic field (Gs) which decides a slice plane of the subject to be examined 1 in any one of X, Y, and Z directions is applied, and to the remaining two directions, a phase encoding gradient magnetic field (Gp) and a frequency encoding gradient magnetic field (Gf) are applied, thereby encoding positional information of each direction in the echo signals. Hereinafter, Gs, Gf, and Gp in combination will be referred to as a gradient magnetic field.

The sending system 5 irradiates an RF pulse so as to excite a nuclear magnetic resonance in a nuclear spin of each atomic element constituting a living tissue of the subject to be examined 1, and the sending system is made up of an RF oscillator 11, a modulator 12, an RF amplifier 13, and an RF coil 14a on the sending side. An RF pulse outputted from the RF oscillator 11 is subjected to an amplitude modulation by the modulator 12 at a time in accordance with a command from the sequencer 4, and subsequently amplified by the RF amplifier 13. Then, the pulse is supplied to the RF coil 14a placed in proximity to the subject to be examined 1, whereby an electromagnetic wave (RF pulse) is irradiated on the subject to be examined 1.

The receiving system 6 detects an echo signal (NMR signal) emitted by the nuclear magnetic resonance in the nuclear spin constituting the living tissue of the subject to be examined 1, and the receiving system is made up of an RE coil 14b on the receiving side, an amplifier 15, a quadrature phase detector 16, and an A/D converter 17. A response electromagnetic wave (NMR signal) from the subject to be examined 1 that is induced by an electromagnetic wave irradiated from the RF coil 14a on the sending side is detected by the RF coil 14b arranged in proximity to the subject to be examined 1, and the NMR signal is amplified by the amplifier 15, and then, divided into orthogonal two-system signals by the quadrature phase detector 16. Thereafter, each signal is converted into a digital amount by the A/D converter 17, and transferred to the signal processing system 7 as data.

It is to be noted that in FIG. 1, the RF coils 14a and 14b on the sending side and on the receiving side, and the gradient magnetic field coils 9 are installed within a static magnetic space of the static magnetic generation system 2 which is located in the space surrounding the subject to be examined 1.

The signal processing system 7 is provided with an external storage device such as an optical disk 19 and a magnetic disk 18, and a display 20 made up of CRT and the like. The signal processing system 7 processes the data received from the receiving system 6 according to a directive from the CPU 8.

The operating part 25 serves as an interface to input various control information necessary for the control within the MRI apparatus, and the operating part is provided with a track ball or a mouse 23, a keyboard 24, and the like. The operating part 25 is disposed in proximity to the display 20, and it is configured such that the operator is allowed, while looking at the display 20, to control various processing of the MRI apparatus interactively via the operating part 25.

The living body signal detector 28 generates pulse waves from living body signals obtained by a device such as an electrocardiac sensor, a sphygmograph sensor, a respiration sensor, and the like, which are installed on the subject to be examined 1, and transmits the pulse waves to the sequencer 4 and the CPU 8.

The sequencer 4 controls application of the RF magnetic field pulse (RF pulse) and the gradient magnetic field pulse, according to a predetermined imaging sequence. The sequencer 4 operates under the control of the CPU 8, and sends various commands necessary for collecting data regarding a tomographic image of the subject to be examined 1, to the sending system 5, the gradient magnetic field generation system 3, and the receiving system 6. Further in the present embodiment, the sequencer 4 executes the predetermined imaging sequence using a pulse wave received from the living body signal detector 28 as a trigger, and achieves an imaging which is gated with the living body signals. In the present embodiment as described below, an explanation will be made, taking an example of imaging gated with an electrocardiogram (ECG), in which the signals acquired by the electrocardiac sensor are used as the living body signals, i.e., the timing of the imaging sequence is gated with the cardiac motion (heartbeat period). Hereinafter, a pulse wave obtained from the living body signal acquired by the electrocardiac sensor will be referred to as "ECG waveform". Further in the present embodiment, as described below, the gradient magnetic field generation system 3 is controlled in such a manner that the frequency encoding gradient magnetic field is applied in the moving direction of the table 26.

The table controller 27 controls the operation of the table 26 according to a command from the CPU 8. In the present embodiment, the movement of the table 26 is controlled, in sync with a control of the imaging by the sequencer 4 in response to the living body signals obtained from the living body signal detector 28. Details of the control will be described below.

The CPU 8 controls the overall operations of the MRI apparatus. In the present embodiment, upon receipt of the data from the receiving system 6, the CPU executes processing such as signal processing and image reconstruction, and displays a tomographic image of the subject to be examined 1, being a result of the processing, on the display 20, and records the result in the external storage device. The CPU further calculates a period of body motion from the living body signals received from the living body signal detector 28, further calculates a table moving speed and/or a table travel distance, considering parameters of the imaging sequence, and outputs a command to the table controller 27.

Currently, a spin species as an imaging target of the MRI apparatus, which is commonly used clinically, is proton being a principal constitutive substance of the subject to be examined 1. In the MRI apparatus, an image is created based on a spatial distribution of proton density and a spatial distribution of relaxation phenomenon of excited state, and morphology such as human head, abdomen, extremities or functions thereof are imaged two-dimensionally or three-dimensionally.

Next, with reference to FIG. 2, a typical imaging sequence for measuring an echo signal will be explained. FIG. 2A shows a gradient echo pulse sequence. RF, Gs, Gp, Gr, and AD/echo in FIG. 2A represent respectively, axes of RF pulse, slice gradient magnetic field, phase encoding gradient magnetic field, frequency encoding gradient magnetic field, and AD conversion/echo signal. The reference numeral 201 represents an RF pulse, 202 represents a slice selective gradient magnetic field pulse, 203 represents a phase encoding gradient magnetic field pulse, 204 represents a frequency encoding gradient magnetic field pulse, 205 represents a sampling window, and 206 represents an echo signal.

The echo signal 206 is repeatedly acquired within a time interval 208 (repetition time TR) starting from the time when the RF pulse 201 is irradiated. The echo signal 206 is generated in such a manner as showing a maximum value after a lapse of time 207 (echo time TE) from the time when the RF pulse 201 is irradiated. The echo signals 206 being acquired are arranged in k-space 209 (which is a space for arranging the acquired echo signals 206 as data; also referred to as "measurement space"). FIG. 2B illustrates a group (at least one echo signal constitutes the group) of echo signals 206-1, 206-2, 206-3, and the like, up to 206-11, which are acquired by repeating the imaging sequence as shown in FIG. 2A, those echo signals being arranged in the measurement space. In here, a length of the arrows in the horizontal axis kx corresponds to the time of the sampling window 205 (sampling interval) of the echo signal 206. The vertical axis ky corresponds to an amount of the phase encoding gradient magnetic field pulse 203.

It is to be noted that in the present embodiment, the imaging sequence to acquire an echo signal is not limited to the example above. For instance, it is possible to apply other types of sequence, such as a single-shot type sequence for acquiring all the data in the phase encoding direction in the measurement space after one single excitation, including a publicly known spin echo pulse sequence, a high-speed spin echo pulse sequence, and a single shot echo planner sequence (EPI), and a multi-shot type sequence such as multi-shot EPI, for acquiring all the data in the phase encoding direction in the measurement space by multiple excitations. Furthermore, another imaging sequence can be applied which performs not only two-dimensional measurement, but also three-dimensional measurement.

Next, a specific example of a general gated imaging will be explained. Figures from FIG. 3A to FIG. 3D are illustrations for explaining an ECG-gated imaging. Each of the reference numerals 301-1 and 301-2 represents an ECG waveform (R-wave) acquired by the living body signal detector 28, and each of the reference numerals 302-1 and 302-2 represents an interval between the ECG waveforms 301-1 and 301-2 (this interval is referred to as "R-R interval" in general. Hereinafter, it is referred to as "R-R interval" or "cardiac cycle"). In the case of the ECG-gated imaging, after a lapse of time intervals 303-1 and 303-2 (hereinafter, the interval is referred to as "delay time", and each delay time 303-1, 303-2, and the like, are set evenly) from the detection of the ECG waveforms 301-1 and 301-2, respectively, a desired number of echo signals are acquired in each of the time intervals 304-1 and 304-2 (a measurement time after a receipt of the ECG waveform 301). Reference numerals 305-1 and 305-2 represent a group of echo signals which are acquired within the time intervals, respectively. This operation is repeated as to each ECG waveform, in order to obtain echo signals necessary for reconstructing one image, gated with the cardiac cycle. It is to be noted that in the explanation below, if there is no need to distinguish in particular by the numbering after a hyphen, the numbers after the hyphen may be omitted.

FIG. 3A illustrates a time chart of the ECG-gated imaging in the case where one image is acquired during the R-R interval 302 between each of the ECG waveforms 301. FIG. 3C illustrates groups of echo signals 305 acquired at the timing shown in FIG. 3A, being arranged in the measurement space. The locations of the echo signals 305 in the measurement space are determined depending on an application amount of the phase encoding gradient magnetic field (phase encoding amount). In the ECG-gated imaging as shown in FIG. 3A, the imaging sequence is executed while varying the phase encoding amount with respect to each ECG waveform 301, in such a manner that the groups of echo signals 305-1, 305-2, and the like, cover all over the measurement space, the groups of the echo signals being obtained by using the ECG waveforms 301-1, 301-2, and the like, respectively as a trigger. Since the echo signals are acquired after a lapse of identical delay time in each cardiac cycle, the measurement space is filled with an identical time phase. By using all the measurement space data being obtained, one piece of image is reconstructed.

It is to be noted that as one example of the ECG-gated imaging, there is an imaging method for obtaining images having different time phases so as to obtain images showing a continuous cardiac motion (typically referred to as a "cine imaging"). FIG. 3B is a time chart of the cine imaging. In this example here, groups of echo signals 306, 307, and the like, up to 30n are obtained during the R-R interval 302 of a single-time ECG waveform 301, and images of multiple time phases are obtained respectively from the groups of echo signals. FIG. 3D illustrates the groups of echo signals 306, 307, and the like, up to 30n obtained at the timing shown in FIG. 3B are arranged in the measurement space.

Also in this case, similar to the process as shown in FIG. 3A, echo signals are acquired within the time interval 304 after a lapse of the delay time 303 from the ECG waveform 301. It is to be noted that the pulse sequence is executed by varying the phase encoding amount with respect to each ECG waveform 301 in such a manner that all over the measurement space is covered as to each of the echo signal groups 306, 307, and the like, up to 30n as shown in FIG. 3D. Accordingly, the measurement space is filled with respectively different time phases. By reconstructing images of the respective time phases, it is possible to obtain an image which displays the cardiac motion continuously.

Next, a general moving table imaging will be schematically explained, the imaging being executed while moving a table on which the subject to be examined 1 is placed. FIG. 4 illustrates the moving table imaging in the case where an imaging plane is set horizontally with respect to the table 501. On the table surface 501, if x-axis is taken in the body axis direction, y-axis is taken in a direction perpendicular to the body axis, and z-axis is taken in a direction perpendicular to the table surface 501, a slice selective gradient magnetic field is applied in the z-axis direction, in the example of FIG. 4. FIG. 4A illustrates the table 501 viewed in the z-axis direction, and FIG. 4B illustrates the table 501 viewed in the y-axis direction. While the imaging is executed, the table 501 moves in the x-axis direction, and the imaging area 502 on the subject to be examined 1 moves relatively in the reverse direction in the x-direction.

In the moving table imaging, a moving direction of the table 501 and a direction for applying the frequency encoding gradient magnetic field are configured to be the same, and echo signals are acquired while recursively varying the phase encoding amount of the imaging sequence in conjunction with the movement of the table 501. The echo signals acquired during the repetition time (TR) of a single time pulse sequence are subjected to one-dimensional Fourier transform in the readout direction (ky-direction), and hybrid data 503 as shown in FIG. 4C can be acquired. In FIG. 4C, the horizontal axis represents a position (x), and the vertical axis represents a phase encoding amount being applied. In FIG. 4C, for ease of explanation, it is assumed that there are eight types of phase encoding amount being applied when the echo signals are acquired.

In the example as shown in FIG. 4C, with the progress of imaging, the table 501 and the subject to be examined 1 fixed on the table 501 move in the x-axis direction. Therefore, the imaging area 502 moves in the reverse direction (from 502-1 to 502-2) relative to the table 501 (and the subject to be examined 1). In the coordinate system fixed to the table 501 (and subject to be examined 1), the data being acquired varies in x-coordinate. On the other hand, since the phase encoding amount varies recursively, when hybrid data 503 (503-1 and 503-9, 503-2 and 503-10, or the like) being acquired in the same phase encoding amount are arranged on the coordinate system of FIG. 4C, with an identical value in the y-axis direction.

On this occasion, the moving speed of the table 501 (table moving speed) is controlled in association with the execution time (for example, repetition time TR) of the imaging sequence, or conversely, the execution time (for example repetition time TR) of the pulse sequence is controlled in association with the table moving speed. Then, as shown in FIG. 4C or FIG. 4D, it is possible to combine the hybrid data 503 without generating discontinuity in the imaging area 502. In other words, the table moving speed V is controlled so that the following formula is satisfied, the hybrid data 503 having the same value in y-axis direction becomes continuous, assuming that the repetition time interval of the imaging sequence as "TR", the number of data acquisition times in the phase encoding (Ky) direction as "phase#", and a field of view size in the readout gradient magnetic field direction as "FOVx":

$$V \leq FOVx/(TR \times phase\#) \quad \text{(Formula 1)}$$

FIG. 4D shows the hybrid data obtained as a result of the control of the table moving speed V as described above. In the same way as FIG. 4C, FIG. 4D also illustrates an example where it is assumed that there are eight types of phase encoding amount being applied when the echo signal is measured. The hybrid data items 504-1, 504-2, and the like, up to 504-8 are obtained respectively, by applying phase encoding amounts being different from one another. The hybrid data items 504 being obtained are subjected to the Fourier transform in the ky-direction, and a final image is obtained.

In the case of the moving table imaging as described above, the imaging area moves with the passage of time. Therefore, it is necessary that a single imaging sequence is performed continuously to bring the hybrid data 504 to completion. In other words, it is difficult to change the imaging sequence in midstream. Therefore, if multiple different imaging sequences are performed such as obtaining multiple images different in contrast, it is necessary that the table is reset to the original position for each imaging sequence, and a similar table movement is repeated. This process will be explained with reference to FIG. 5.

FIG. 5(a) illustrates a time chart for the case where, while the table is moved, multiple types of imaging using different imaging sequences are performed individually, the imaging being performed so as to obtain multiple images having contrast different from one another. While the table speed is controlled as explained with reference to FIG. 4, each of the imaging sequences; measurement 1 (601-1), measurement 2 (601-2), measurement 3 (601-3), and the like, are performed individually. FIG. 5(b) illustrates the positions of the table 501 with the passage of time, when each of the measurements 601-1, 601-2, and 601-3 as shown in FIG. 5(a) are performed. In the example here, in a coordinate system fixed in imaging space, which is an xyz coordinate system having the axes respectively in the same directions as FIG. 4, a center position of the table 501 in the x-direction (referred to as a "position of the table 501") at the time of starting the measurement is assumed as zero. The position of the table 501 moves only by a distance corresponding to a full width of the imaging range 502 in the x-axis direction, in the body axis direction (x-axis direction) along with the progress of the measurement 601-1 (602). Thereafter, the table is reset to the position at the point when the measurement is started (603). In order to obtain images of the same portion different in contrast respectively by the measurements (601-1, 601-2, and 601-3), the table 501 is reset to the same position for each starting of the measurements, and the same operation is repeated.

When multiple types of imaging sequences are performed as described above, the table has to be put back every single time, if the moving table imaging is simply combined. Therefore, this may reduce efficiency, taking time for the imaging. Moreover, if the gated imaging is combined with the configuration above so as to reduce an artifact, a waiting time of the gated imaging is also added, and it may take longer time for the imaging.

In the present embodiment, in order to achieve a more efficient imaging, multiple different imaging sequences are executed individually within a predetermined time interval. The table is not moved continuously but kept unmoved while acquiring echo signals within every single time interval, and after the signal acquisition is finished, the table is moved during the time until the next time interval.

Hereinafter, in the present embodiment, an explanation will be made taking an example that a predetermined time interval is assumed as a cardiac cycle according to a single ECG waveform. In other words, within a single cardiac cycle, the multiple different imaging sequences are executed individually. The table is not moved while acquiring echo signals, and after the signal acquisition is finished, the table is moved during the time interval until a receipt of next ECG waveform. In the present embodiment, an explanation will be made, taking an example in which multiple different imaging sequences to be executed within a cardiac cycle according to a single ECG waveform is assumed as the imaging sequences that allow acquisition of images different in contrast respectively. In the present embodiment, both the phase encoding amount to be applied and the number of echo signals acquired within a single cardiac cycle are the same for each of the imaging sequences to be executed.

FIG. 6 illustrates an overview of the imaging according to the present embodiment. In here, an explanation will be made taking as an example in which three different imaging sequences are executed. FIG. 6A shows a time chart (signal acquisition procedure) of the imaging according to the present embodiment. In the present embodiment, after a lapse of delay time 701-1 from the ECG waveform 301-1, the measurement (705-1) of a predetermined number of echo signals is performed by the imaging sequence 705. After a lapse of delay time 702-1 from the ECG waveform 301-1, the measurement (706-1) of a predetermined number of echo signals is performed by the imaging sequence 706. After a lapse of delay time 703-1 from the ECG waveform 301-1, the measurement (707-1) of a predetermined number of echo signals is performed by the imaging sequence 707. Thereafter, from the ECG waveform 301-2, each of the imaging sequences is repeated in the similar manner. It is to be noted that the reference numeral 704-1 indicates a measurement time according to the ECG waveform 301-1, and the reference numeral 704-2 indicates a measurement time according to the ECG waveform 301-2.

The groups of echo signals acquired in each of the measurements according to the process above are arranged in the measurement space as to each of the imaging sequences as indicated by the reference numerals 708, 709, and 710 in FIG. 6B. The echo signal groups obtained by the measurements 705-1 and 705-2, 706-1 and 706-2, 707-1 and 707-2 in each of the imaging sequences 705, 706, and 707 are of the imaging sequences to obtain images different in contrast respectively as described above. Therefore, the measurement spaces are generated independently for the respective sequences. In the present embodiment, as described above, both the phase encoding amount being applied and the number of echo signals acquired during the measurement zone 704 of a single time ECG waveform 301 are the same in each of the imaging sequences 705, 706, 707, and the like. Therefore, the data items obtained in each of the imaging sequences are arranged in the same width in the ky-direction of each of the measurement spaces 708, 709, 710, and the like.

On this occasion, as explained in FIG. 4, in order to obtain continuous hybrid data from each of the imaging sequences, the table travel distance D during the cardiac cycle 302 is intended to be equal to or less than the right-hand side of the following formula (Formula 2).

$$D \leq FOVmin/(Phase\#/PN) \quad \text{(Formula 2)}$$

Here, "FOVmin" represents a minimum value of FOV size in the frequency encoding gradient magnetic field direction within each of the imaging sequences, "Phase#" represents the phase encoding number, and "PN" represents the number of echoes in each of the imaging sequences obtained according to a single ECG waveform 301 (i.e., the number of echoes obtained in each of the sequences 705, 706, and 707).

FIG. 6C shows a state of the hybrid data that is obtained in the imaging sequence 705 in the case where the table travel distance D is controlled in such a manner as satisfying the Formula 2. The hybrid data obtained by the other imaging sequences 706 and 707 are illustrated in the similar manner.

In the present embodiment, using each ECG waveform 301 as a trigger, echo signals with the same encoding amount are acquired as to all the imaging sequences, and an operation to control the table movement as described above is repeated. Consequently, images of respective imaging sequences are obtained.

Next, according to the time chart as shown in FIG. 6A, an imaging control by the CPU 8 will be explained, which allows an acquisition of multiple images different in contrast. FIG. 7 is a process flow of the imaging control by the CPU 8 according to the present embodiment. The imaging control processing in the present embodiment includes three processes; an imaging parameter setting process 110, a signal measurement and table moving process 120, and an image reconstruction process 130.

The imaging parameter setting process 110 includes an imaging sequence designation step 111, a gated imaging condition setting step 112, and a preprocessing step 113.

In the imaging sequence designation step 111, a designation is accepted regarding the number of imaging sequences to be executed in the MRI apparatus and the imaging parameters for each of the imaging sequences. In addition, in the gated imaging condition setting step 112, inputting of various parameters for the gated imaging is accepted as to each of the imaging sequences which are accepted in the imaging sequence designation step 111. It is to be noted that various inputting in the imaging sequence designation step 111 and the gated imaging condition setting step 112 is performed via the input screen 1101, which is displayed on the display 20, and the operation part 25.

FIG. 8 shows one example of the input screen 1101 for accepting an input from a user, which is displayed on the display 20. The input screen 1101 of the present embodiment is provided with a heart beat rate input area 1102 for accepting an input of heart rate, an imaging sequence number input area 1103 for accepting an input of imaging sequences number, an imaging parameter input area 1104 for accepting an input of the imaging parameter of each of the imaging sequences, and a gated imaging time input area 1105 for accepting an input of timing for executing each of the imaging sequences in association with an ECG waveform.

It is to be noted that the CPU 8 generates the imaging parameter input area 1104 according to the number of imaging sequences, which is accepted in the imaging sequence number input area 1103. By way of example, when inputting of the imaging sequences number is accepted via the imaging sequence number input area 1103, the CPU 8 provides a sequence number in such a manner that the imaging parameter can be set with respect to each of the imaging sequences, the number of which corresponds to the imaging sequence number being accepted. Then, the respective sequence numbers are displayed in a form of tabs. Afterwards, selection of each tab is accepted, enabling an input of the imaging parameters for each of the imaging sequences.

As the imaging parameters, inputting of following items are accepted for example; a type of sequence "Sequence", a field of view "FOV", a repetition time "TR", an echo time "TE", a slice number "Slice#", a slice thickness "Thickness", a slice gap "Slice gap", a flip angle "FA", a frequency encoding number "Freq#", a phase encoding number "Phase#", a reconstruction "Recon", and the number of signals averaged "NSA". It is to be noted that in the present embodiment, in order to acquire images different in contrast by the respective imaging sequences, inputting of the repetition time TR and the echo time TE being different for each image, are accepted. In the present embodiment, the phase encoding amount to be applied in each of the imaging sequences is identical. Therefore, as to the phase encoding number Phase#, inputting of a value being the same for each imaging sequence is accepted. The imaging parameter whose inputting is accepted here is reflected in the gated imaging time input area 1105.

In the gated imaging time input area 1105, as to each imaging sequence, there are accepted inputs of delay time 1106 in association with the ECG waveform, and the number of echo signals (echo number) 1107 being acquired by using a single time ECG waveform as a trigger. In the present embodiment, the echo number 1107 is assumed to be the same in all the imaging sequences, and therefore, it is possible to configure such that the echo number is inputted only for the first imaging sequence. Hereinafter, an explanation will be made on that premise.

In the present embodiment, inputting of the delay time 1106 is accepted sequentially from the imaging sequence having the smallest number among the sequence numbers being given. In the present embodiment, the echo number to be acquired during a single cardiac cycle as to each imaging sequence is assumed to be the same, inputting of the echo number 1107 is also accepted for the first imaging sequence. When the CPU 8 accepts inputting of the delay time 1106 for each of the imaging sequences, a total time length necessary for the imaging sequences is calculated based on the R-R interval being calculated from the number of heart beats 1102 and other imaging parameters, inputting of which has been accepted in the imaging sequence designation step 111. Then, it is determined whether or not the acceptance of input is possible. By way of example, if the imaging sequence executed in advance has not been completed yet within the delay time 1106 being inputted, or if acquisition of the echo number 1107 cannot be completed within the R-R interval in the case where processing is started after the lapse of the delay time 1106 being inputted, such situation is notified, and the acceptance is denied. Alternatively, the maximum number of echoes which can be inputted may be set automatically.

It is further possible to configure such that inputting of the delay time 1106 is allowed to be accepted only for the imaging sequence which is executed initially. In the case above, the subsequent imaging sequences, starting from the second time, are executed just after the completion of the precedent imaging sequence. When the delay time 1106 and the echo number 1107 are inputted for the first imaging sequence, a time length is calculated which is required for all the imaging sequences, and the time is compared with the R-R interval having already been calculated. Then, an executable imaging sequence is determined.

As shown in FIG. 8, in the present embodiment, there is shown an example that a window dedicated to be used as an input screen 1101 is provided. However, it is not necessarily provide an independent window. As for the screen configuration, there is no restriction such as making the input screen 1101 to be the same as shown in FIG. 8. Any other configuration may be applicable if it allows necessary parameters to be inputted in the light of the purpose of the present invention.

Upon accepting inputs as described above via the input screen 1101, in the imaging sequence designation step 111 and in the gated imaging condition setting step 112, the CPU 8 calculates the number of repetitions L of the cardiac cycle and the table travel distance D, based on each of the parameters being inputted (preprocessing step 113).

Here, the number of repetitions L of the cardiac cycle corresponds to the number of cardiac cycles necessary for acquiring all the data necessary for reconstructing an image within a desired range of a subject to be examined. The number of repetitions L is calculated by using the phase encoding number Phase# and the echo number 1107. The table travel distance D during the cardiac cycle is determined based on the FOV of each imaging sequence, according to the Formula 2.

Once the imaging sequence to be executed is decided definitely, the CPU performs the signal measurement and table moving process 120.

In the signal measurement and table moving process 120, the CPU 8 constructs an imaging sequence by using various parameters being inputted in the imaging parameter setting process 110, and allows the sequencer 4 to perform the measurement.

The measurement is executed, gated with the ECG waveform. Therefore, the sequencer 4 firstly initializes the counter 1, which counts the number of ECG waveforms being transmitted from the living body signal detector 28 (step 121). Subsequently, upon receipt of an ECG waveform (step 122), the sequencer 4 updates the counter 1 of the ECG waveform (incremented by one) (step 123), executes each of the imaging sequences after a lapse of the delay time 1106 from the ECG waveform, as to each of the imaging sequences being inputted, and measures a predetermined number of groups of echo signals (step 124). The echo signals being detected are arranged in the measurement space. Then, the CPU 8 issues a command to the table controller 27 so that the table is moved by the distance D which is calculated in the preprocessing step 113 (step 125).

After the execution of all the imaging sequences, which are executed using a single ECG waveform as a trigger, the sequencer 4 determines whether or not the counter 1 of the ECG waveform has reached the number of repetitions L in the preprocessing step 113 (step 126). If the counter 1 has not reached the number of repetitions L, the processing returns to step 122. On the other hand, if it has reached the number of repetitions L, the sequencer 4 notifies the CPU 8 that the measurement is finished. The CPU 8 that has received the notification allows the processing to proceed with the image reconstruction process 130.

In the image reconstruction process 130, the CPU 8 allows the signal processing system 7 to process the data items. The signal processing system 7 combines the obtained data items with respect to each of the imaging sequences (step 131), subjects the data items to Fourier transform to generate images (step 132), and displays the images on the display 20 (step 133).

As discussed above, the magnetic resonance imaging apparatus according to the present embodiment incorporates the sequencer 4 being an imaging control means for executing an imaging sequence to image a desired area of a subject to be examined 1, the CPU 8 operating as a signal processing means for reconstructing an image from the signals obtained from a result of executing the imaging sequence, and the table controller 27 for controlling movement of the table 26 on which the subject to be examined is placed. The sequencer 4 being the imaging control means executes multiple imaging sequences while the table controller 27 moves the table 26 from a desired first position to a desired second position with the passage of time, and the CPU 8 being the signal processing means reconstructs images respectively by the multiple sequences as to an area from the first position to the second position, using the signals obtained as a result of executing each of the multiple imaging sequences.

In addition, the sequencer 4, being the imaging control means of the magnetic resonance imaging apparatus of the present embodiment, executes the multiple imaging sequences in a predetermined order.

In addition, the sequencer 4, being the imaging control means of the magnetic resonance imaging apparatus of the present embodiment, executes the multiple imaging sequences in the predetermined order, thereby acquiring multiple echo signals for obtaining the multiple images.

In the magnetic resonance imaging apparatus of the present embodiment, at least one echo signal is collected for constituting a part of the measurement space for reconstructing the multiple images, by the respective multiple imaging sequences which are executed in the predetermined order.

It is to be noted that the desired first position indicates a position where a desired first portion of the subject to be examined 1 is placed within the imaging space, and the desired second position indicates a position where a desired second portion of the subject to be examined 1 is placed within the imaging space.

Here, the first portion may be a head region of the subject to be examined 1, and the second portion may be a foot region of the subject to be examined 1.

The images obtained with respect to each of the multiple sequences may include images different in contrast.

In the magnetic resonance imaging apparatus of the present embodiment, a moving speed of the table 26, which is controlled by the table controller 27, is set to be equal to or lower than a desired first speed which allows a collection of multiple echo signals being sufficient for reconstructing images as to the regions of the subject to be examined 1 respectively.

In other words, the first speed indicates a speed which satisfies the following: (Travel distance of the table 26 during the time interval for executing one set of multiple sequences in the predetermined order)=(Minimum value of FOV (FOVmin))/(Total phase encoding number (Phase#)/Number of echoes (PN) acquired by one set of multiple sequences executed in the predetermined order).

The sequencer 4 being the imaging control means of the magnetic resonance imaging apparatus according to the present embodiment exercises control in such a manner that the frequency encoding gradient magnetic field is applied in the moving direction of the table 26.

In addition, the magnetic resonance imaging apparatus of the present embodiment further incorporates a living body information detector 28 for acquiring a periodic body motion of the subject to be examined 1, and the sequencer 4 being the imaging control means may be configured in such a manner that the multiple imaging sequences are executed, gated with the body motion period of the subject to be examined 1, which is detected by the living body information detector 28.

In the magnetic resonance imaging apparatus of the present embodiment in which the sequencer 4 being the imaging control means, executes the multiple imaging sequences, gated with the body motion period of the subject to be examined 1, which is detected by the living body information detector 28, the sequencer 4 being the imaging control means, has control so that at least two imaging sequences are executed during a single period of body motion of the subject to be examined 1, which is detected by the living body information detector 28.

It is to be noted that in the magnetic resonance imaging apparatus of the present embodiment in which the sequencer 4 being the imaging control means executes the multiple imaging sequences, gated with the body motion period of the subject to be examined 1, which is detected by the living body information detector 28, the sequencer 4 being the imaging control means has control so that all the multiple imaging sequences are executed during a single period of the body motion of the subject to be examined 1, which is detected by the living body information detector 28.

In the magnetic resonance imaging apparatus of the present embodiment in which the sequencer 4, being the imaging control means, executes the multiple imaging sequences gated with the body motion period of the subject to be examined 1, which is detected by the living body information detector 28, the moving speed of the table 26 controlled by the table controller 27 is set to be equal to or lower than a desired second speed which allows a collection of a group of echo signals being sufficient for reconstructing images for the respective regions of the subject to be examined 1.

It is to be noted that the second speed indicates a speed which satisfies the following: (Travel distance of the table 26 during the body motion period)=(Minimum value of FOV)/(Total phase encoding number/Number of echoes acquired during the body motion period).

After execution of the multiple imaging sequences within the predetermined time interval, the table controller 27 of the magnetic resonance imaging apparatus of the present embodiment moves the table 26 by a predetermined distance being equal to or lower than the minimum value of FOV, in the table moving direction of the table 26.

As discussed above, in the present embodiment, an identical encoding amount is applied to each of the multiple imaging sequences and those imaging sequences are executed for a predetermined time interval, e.g., at a single cardiac cycle, thereby acquiring echo signals, the number of which is identical in each of the imaging sequences. In addition, the table is moved in the frequency encoding direction gated with the cardiac cycle, so that the data items of the respective imaging sequences become continuous in the hybrid space. Therefore, according to the present embodiment, only a single time table movement allows an execution of the multiple imaging sequences gated with the electrocardiogram, and images can be reconstructed according to the results of the multiple imaging sequences, respectively.

In other words, according to the present embodiment, when multiple types of imaging in a wide range are performed, it is possible to shorten the overall imaging time, while reducing an artifact, thereby enhancing an efficiency of the imaging. In other words, a high quality image can be obtained in a short period of time. Since it is not necessary to put back the table every single time, cumbersome operations can be reduced.

According to the present embodiment, since multiple sequences are executed almost simultaneously, while the table is moved, it facilitates a comparison of multiple images, when the obtained multiple images are compared in overlapping manner. By way of example, when a different imaging sequence is executed by resetting the table every single time, the subject to be examined may move while the table is put back, and displacement in position of the subject to be examined may occur, degrading the comparison of overlapping multiple images. However, according to the present embodiment, it is possible to reduce such inconvenience.

<Second Embodiment>

Next, a second embodiment of the present invention will be explained with reference to the accompanying drawings. In the first embodiment, multiple imaging sequences are executed during the R-R interval after a single ECG waveform, for obtaining images different in contrast. On the other hand, in the present embodiment, such imaging sequences are executed across multiple R-R intervals. In other words, in the present embodiment, an explanation will be made by taking an example that the number of cardiac cycles used as a unit for executing multiple imaging sequences (hereinafter, referred to as "unit cardiac cycle") is two times. The configuration of the MRI apparatus according to the present embodiment is basically the same as that of the first embodiment. Therefore, detailed explanations will not be made inhere. Hereinafter, the present invention will be explained, putting importance on a point which is different from the first embodiment.

FIG. 9 illustrates an overview of the imaging (signal acquisition) according to the present embodiment. FIG. 9A shows a time chart (signal acquisition procedure) of the imaging according to the present embodiment. FIG. 9B shows a state that the groups of echo signals acquired by the measurements are arranged in the measurement space with respect to each of the imaging sequences.

In the present embodiment, as to each of four different imaging sequences 803, 804, 808, and 809, the imaging sequences 803 and 804 are executed within the measurement time 805 after receipt of a single ECG waveform 301-1, and the imaging sequences 808 and 809 are executed within the measurement time 810 after a receipt of the next ECG waveform 301-2. Specifically, after a lapse of delay time 801-1 from the ECG waveform 301-1, the measurement (803-1) of a predetermined number of echo signals is performed by the imaging sequence 803. After a lapse of delay time 802-1 from the ECG waveform 301-1, the measurement (804-1) of a predetermined number of echo signals is performed by the imaging sequence 804. Next, after a lapse of delay time 806-1 from the ECG waveform 301-2, the measurement (808-1) of a predetermined number of echo signals is performed by the imaging sequence 808. In addition, after a lapse of delay time 807-1 from the ECG waveform 301-2, the measurement (809-1) of the predetermined number of echo signals is performed by the imaging sequence 809, and from the ECG waveform 301-3, each imaging sequence is repeated in the similar manner. It is to be noted that the reference numeral 805-1 indicates a measurement time according to the ECG waveform 301-1, and the reference numeral 810-1 indicates a measurement time according to the ECG waveform 301-2. It is a matter of course that the number of the imaging sequences to be executed is not limited to the example above.

Also in the present embodiment, in a similar manner as the first embodiment, various imaging sequences are prepared to obtain images different in contrast respectively, and both the number of echo signals acquired during the unit cardiac cycle and the phase encoding amount to be applied are the same in each of the imaging sequences.

FIG. 9B illustrates a state where groups of echo signals being acquired are arranged in the measurement space as to each of the imaging sequences. Since both the phase encoding amount to be applied and the number of echo signals are the same in each of the imaging sequence, it is possible to obtain data within the same range in the ky-direction as to each of the imaging sequences during the unit cardiac cycle.

In the present embodiment, in order to acquire the data items within the same range in the ky-direction as to all of the imaging sequences during two cardiac cycles, the table is controlled to move only by the distance D' during the two cardiac cycles. For the operation above, there is a method to move the table by the distance D' every two cardiac cycles, and there is another method to move the table by the distance D=D'/2 every single cardiac cycle. In the present embodiment, an explanation will be made, taking the latter method as an example.

In other words, it is assumed that the table travel distance D during a single cardiac cycle satisfies the following Formula 3, so that the hybrid data obtained from each of the imaging sequences becomes continuous:

$$D \leq FOV\text{min}/(\text{Phase\#}/PN \times P) \quad \text{(Formula 3)}$$

Here, "FOVmin" represents a minimum value of FOV size in the frequency encoding gradient magnetic field direction within each of the imaging sequences, "Phase*" represents a phase encoding number, "PN" represents the number of echoes in each of the imaging sequences obtained according to a single ECG waveform 301 (i.e., the number of echoes obtained in each of the sequences 803, 804, 808, and 809), and "P" represents the number of body motion periods required for executing all the imaging sequences as one set.

In the present embodiment, the same number of echo signals are acquired with the same phase encoding amount as to all the imaging sequences during the R-R period, after a receipt of each of the ECG waveforms 301-1 and 301-2, while the table movement is controlled as described above, and the operation is repeated, thereby obtaining images of the respective imaging sequences.

Next, an imaging control by the CPU 8 will be explained, for acquiring multiple images different in contrast respectively, according to the time chart as shown in FIG. 9A. FIG. 10 shows a process flow of the imaging control performed by the CPU 8 according to the present embodiment. In the same manner as the first embodiment, the imaging control process of the present embodiment includes three processes, an imaging parameter setting process 210, a signal measurement and table moving process 220, an image reconstruction process 230.

The imaging parameter setting process 210 includes an imaging sequence designation step 211, a gated imaging condition setting step 212, and a preprocessing step 213. In the same manner as the first embodiment, in the imaging sequence designation step 211 and in the gated imaging condition setting step 212, inputting of the followings from a user is accepted via the input screen 1101 and the operation part 25; the number of each of the imaging sequences, imaging parameters for the respective sequences, the delay time 1106 for each of the ECG waveforms, the number of echo signals (echo number) 1107 being acquired using a single time ECG waveform as a trigger.

Also in the present embodiment, inputting of the delay time 1106 is accepted sequentially from the first imaging sequence. As for the first imaging sequence, inputting of the echo number 1107 is further accepted. When the CPU 8 accepts inputting of the delay time 1106 for each of the imaging sequences, a total time length necessary for the imaging sequences is calculated based on the R-R interval being calculated from the number of heart beats 1102 and other imaging parameters, inputting of which has been accepted in the imaging sequence designation step 211. Then, it is determined whether or not the acceptance of input is possible. By way of example, if the imaging sequence executed in advance has not been completed yet within the delay time 1106 being inputted, such situation is notified, and the acceptance is denied. Alternatively, the number of echoes which can be inputted may be set automatically.

If it is determined that acquisition of the echo number cannot be completed within the R-R interval in the case where processing is started after the lapse of the delay time being inputted, the CPU 8 makes a notification of the situation. With the notification, the user inputs once again the delay time 1106 so that the imaging sequence is executed in the next cardiac cycle. As shown in FIG. 8, it is possible to configure such that in the gated imaging time input area 1105, the imaging sequences are displayed with respect to each of the cardiac cycles, in which the imaging sequences are executed. In the present embodiment, it is assumed that all the imaging sequences are executed by using two cardiac cycles, but this is not an exclusive example. It is further possible to configure such that the number of cardiac cycles is increased so that all the imaging sequences can be set.

When the inputting as described above is accepted via the input screen 1101 in the imaging sequence designation step 211 and in the gated imaging condition setting step 212, the CPU 8 calculates the number of repetitions L of the cardiac cycle, the number of repetitions P of the second cardiac cycle, and the table travel distance D (preprocessing step 213) in the similar manner as the first embodiment.

When a necessary calculation is completed, the CPU 8 performs the signal measurement and table moving process 220.

In the signal measurement and table moving process 220, the CPU 8 constructs the imaging sequences by using various parameters inputted in the imaging parameter setting process 101, and allows the sequencer 4 to perform the measurement.

The measurement is executed, gated with the ECG waveform. Therefore, the sequencer 4 firstly initializes the counters 1 and p to count the number of ECG waveforms, which are transmitted from the living body signal detector 28 (step 221, 222). In here, "l" represents a counter to count the number of the cardiac cycle L, and "p" represents a counter to count the number of the unit cardiac cycle P (it is "two" in the present embodiment).

Subsequently, when an ECG waveform is received (step 223), the counter p of the ECG waveform is updated (incremented by one) (step 224), each of the imaging sequences is executed after a lapse of the delay time 1106 of each inputted imaging sequence from the ECG waveform, and then echo signals are detected (step 225). Detected echo signals are arranged in the measurement space. In addition, the CPU 8 issues a command to the table controller 27 so that the table is moved only by the distance D which is calculated in the preprocessing step 213 (step 226).

The sequencer 4 determines whether or not the counter p has reached P (step 227). If it has not reached P yet, the processing returns to step 223. On the other hand, if the counter p has already reached P, the counter 1 is updated (incremented by one) (step 228), and it is determined whether or not the counter 1 has reached the number of repetitions L which is calculated in step 213 (step 229). If the counter 1 has not reached L yet, the processing returns to step 222. On the other hand, if the counter 1 has reached L, the CPU 8 is notified that the measurement is completed. Upon receipt of the notification, the CPU 8 proceeds with the image reconstruction process 230.

In the image reconstruction process 230, the CPU 8 allows the signal processing system 7 to process data. The signal processing system 7 combines the obtained data items, with respect to each type of the imaging sequence (step 231), subjects the data items to the Fourier transform to generate images (step 232), and displays the images on the display 20 (step 233).

As discussed above, the magnetic resonance imaging apparatus according to the present embodiment incorporates the sequencer 4 being an imaging control means for executing an imaging sequence to image a desired area of a subject to be examined 1, the CPU 8 operating as a signal processing means for reconstructing an image from the signals obtained from a result of executing the imaging sequence, and the table controller 27 for controlling movement of the table 26 on which the subject to be examined is placed. The sequencer 4 being the imaging control means executes multiple imaging sequences while the table controller 27 moves the table 26 from a desired first position to a desired second position with the passage of time, and the CPU 8 being the signal processing means reconstructs images respectively by the multiple sequences as to an area from the first position to the second position, using the signals obtained as a result of executing each of the multiple imaging sequences.

The sequencer 4 being the imaging control means of the magnetic resonance imaging apparatus according to the present embodiment executes the multiple imaging sequences in a predetermined order.

The sequencer 4 being the imaging control means of the magnetic resonance imaging apparatus according to the present embodiment executes the multiple imaging sequences in the predetermined order, thereby acquiring multiple echo signals so as to obtain the multiple images.

In the magnetic resonance imaging apparatus of the present embodiment, at least one echo signal is collected for constituting a part of the measurement space for reconstructing the multiple images, by the respective multiple imaging sequences which are executed in the predetermined order.

It is to be noted that the desired first position indicates a position where a desired first portion of the subject to be examined 1 is placed in the imaging space, and the desired second position indicates a position where a desired second portion of the subject to be examined 1 is placed in the imaging space.

Here, the first portion may be a head region of the subject to be examined 1, and the second portion may be a foot region of the subject to be examined 1.

In addition, the images obtained respectively from the multiple sequences may include images different in contrast.

In the magnetic resonance imaging apparatus of the present embodiment, a moving speed of the table 26, which is controlled by the table controller 27, is set to be equal to or lower than a desired first speed which allows a collection of multiple echo signals being sufficient for reconstructing images as to the regions of the subject to be examined 1 respectively.

In other words, the first speed indicates a speed which satisfies the following: (Travel distance of the table 26 during the time interval for executing one set of multiple sequences in the predetermined order)=(Minimum value of FOV (FOVmin))/(Total phase encoding number (Phase#)/Number of echoes (PN) acquired by one set of multiple sequences executed in the predetermined order).

The sequencer 4 being the imaging control means of the magnetic resonance imaging apparatus according to the present embodiment has control so that the frequency encoding gradient magnetic field is applied in the moving direction of the table 26.

In addition, the magnetic resonance imaging apparatus of the present embodiment further incorporates a living body information detector 28 for acquiring a periodic body motion of the subject to be examined 1, and the sequencer 4 being the imaging control means may be configured in such a manner that the multiple imaging sequences are executed, gated with the body motion period of the subject to be examined 1, which is detected by the living body information detector 28.

In the magnetic resonance imaging apparatus of the present embodiment in which the sequencer 4 being the imaging control means, executes the multiple imaging sequences gated with the body motion period of the subject to be examined 1, which is detected by the living body information detector 28, the sequencer 4 being the imaging control means, has control so that at least two imaging sequences are executed during a single period of body motion of the subject to be examined 1, which is detected by the living body information detector 28.

It is to be noted that in the magnetic resonance imaging apparatus of the present embodiment in which the sequencer 4 being the imaging control means executes the multiple imaging sequences gated with the body motion period of the subject to be examined 1, which is detected by the living body information detector 28, the sequencer 4 being the imaging control means, has control so that all the multiple imaging sequences are executed during at least two periods of the body motion of the subject to be examined 1, which is detected by the living body information detector 28.

In the magnetic resonance imaging apparatus of the present embodiment in which the sequencer 4, being the imaging control means, executes the multiple imaging sequences gated with the body motion period of the subject to be examined 1, which is detected by the living body information detector 28, the moving speed of the table 26 controlled by the table controller 27 is set to be equal to or lower than a desired second speed which allows a collection of a group of echo signals being sufficient for reconstructing images for the respective regions of the subject to be examined 1.

It is to be noted that the second speed indicates a speed which satisfies the following: (Travel distance of the table 26 during the body motion period)=(Minimum value of FOV)/(Total phase encoding number/Number of echoes acquired during the body motion period×Number of body motion periods required for executing all of one set of imaging sequences).

After execution of the multiple imaging sequences within the predetermined time interval, the table controller 27 of the magnetic resonance imaging apparatus of the present embodiment moves the table 26 by a predetermined distance being equal to or lower than the minimum value of FOV, in the table moving direction of the table 26.

As discussed above, in the present embodiment, each of the multiple imaging sequences is executed during a unit cardiac cycle with an identical encoding amount being applied, thereby acquiring echo signals, the number of which is identical for each of the sequences. In addition, the table is moved in the frequency encoding direction gated with the unit cardiac cycle, so that the data items by the respective imaging sequences become continuous in the hybrid space. Therefore, according to the present embodiment, only a single time table movement allows an execution of the multiple imaging sequences gated with the electrocardiogram, and images can be reconstructed according to the results of the multiple imaging sequences, respectively.

In other words, according to the present embodiment, when multiple types of imaging for a wide range are performed while the table is moved, it is possible to reduce an artifact with shortening of total imaging time length. That is, a high quality image can be obtained within a short period of time. Since it is not necessary to put back the table every single time, cumbersome operations can be reduced. Further in the present embodiment, compared to the first embodiment, there is an advantage that much more imaging sequences can be executed during a single time table movement. Since there is less time-wise restriction, greater flexibility may be offered in setting imaging parameters.

<Third Embodiment>

Next, a third embodiment will be explained with reference to the accompanying drawings. In the same manner as the second embodiment, when a gated imaging is performed by using multiple cardiac cycles while the table is moved, multiple imaging sequences are executed to obtain various contrast during a single cardiac cycle, and in addition, another imaging sequences are executed for obtaining images different in morphology during the other single cardiac cycle. The configuration of the MRI apparatus according to the present embodiment is basically the same as those explained in the embodiments above. Therefore, detailed explanation will not be made in here. Hereinafter, the present invention will be explained, putting importance on a point which is different from the first embodiment.

FIG. 11 illustrates an overview of the imaging (signal acquisition) according to the present embodiment. FIG. 11A shows a time chart (signal acquisition procedure) of the imaging according to the present embodiment. FIG. 11B shows a state that the groups of echo signals acquired by the measurements are arranged in the measurement space with respect to each of the imaging sequences.

In the present embodiment, three different imaging sequences 903, 904, and 907 are subjected to the ECG-gated imaging. The imaging sequences 903 and 904 are imaging sequences to obtain images having contrast being different one from another. The imaging sequence 907 is an imaging sequence of cine imaging for obtaining images of multiple time phases during one cardiac cycle. It is to be noted that also in the present embodiment, in the same manner as each of the embodiments described above, both the number of echo signals acquired during the unit cardiac cycle and the phase encoding amount to be applied are identical as to each of the imaging sequences. In addition, for the sequence of cineradiography, both the number of echo signals being acquired and the phase encoding amount to be applied are the same as to each of the time phases.

As shown in FIG. 11A, after a lapse of delay time 901-1 from the ECG waveform 301-1, the first measurement (903-1) is performed by the imaging sequence 903. After a lapse of delay time 902-1 from the ECG waveform 301-1, the first measurement (904-1) is performed by the imaging sequence 904, and after a lapse of delay time 906-1 from the ECG waveform 301-2, the first measurement (907-1) is performed by the imaging sequence 907. After a lapse of delay time 901-1 from the ECG waveform 301-3, the second measurement (903-2) is performed by the imaging sequence 903, after a lapse of delay time 902-1 from the ECG waveform 301-3, the second measurement (904-2) is performed by the imaging sequence 904, and after a lapse of delay time 906-1 from the ECG waveform 301-4, the second measurement (907-2) is performed by the imaging sequence 907. The processing above is repeated until the measurement is performed for the number of times corresponding to the number of echoes required for reconstructing images. It is to be noted that in the cine imaging, the cardiac time phase is divided into N, and each is subjected to the measurement. The measurements in the respective time phases are assumed as from 907-1-1, 907-1-2, and the like, up to 907-1-N. In every single time phase, a group of echo signals are obtained, the number of which is the same as that of the other imaging sequences. Data items are arranged for each of the time phases in the measurement space 911, thereby generating N pieces of images.

As shown in FIG. 11B, the data items being acquired are arranged in the same width in the ky-direction, respectively in the measurement spaces 909, 910, 911-1, 911-2, and the like, up to 911-N. In the present embodiment, the data items within the same range in the ky-direction are acquired during two cardiac cycles as to all the imaging sequences. Therefore, the travel distance D of the table is controlled to satisfy the formula of the second embodiment (Formula 3). It is to be noted that P in the Formula 3 is assumed as 2.

In the present embodiment, the same number of echo signals are acquired with the same phase encoding amount as to all the imaging sequences during the R-R period after a receipt of each of the ECG waveforms 301-1 and 301-2, while the operation for controlling the table to move by the distance D is repeated, whereby images of respective imaging sequences are obtained.

Since the control of imaging according to the time chart of FIG. 11A is the same as the second embodiment, tedious explanation will not be made here.

As discussed above, the magnetic resonance imaging apparatus according to the present embodiment incorporates the sequencer 4 being an imaging control means for executing an imaging sequence to image a desired area of a subject to be examined 1, the CPU 8 operating as a signal processing means for reconstructing an image from the signals obtained from a result of executing the imaging sequence, and the table controller 27 for controlling movement of the table 26 on which the subject to be examined is placed. The sequencer 4 being the imaging control means executes multiple imaging sequences while the table controller 27 moves the table 26 from a desired first position to a desired second position with the passage of time, and the CPU 8 being the signal processing means reconstructs images respectively for the multiple sequences as to an area from the first position to the second position, by using the signals obtained as a result of executing each of the multiple imaging sequences.

In addition, the sequencer 4 being the imaging control means of the magnetic resonance imaging apparatus according to the present embodiment executes the multiple imaging sequences in a predetermined order.

The sequencer 4 being the imaging control means of the magnetic resonance imaging apparatus according to the present embodiment executes the multiple imaging sequences in the predetermined order, thereby acquiring multiple echo signals so as to obtain the multiple images.

In the magnetic resonance imaging apparatus of the present embodiment, at least one echo signal is collected for constituting a part of the measurement space for reconstructing the multiple images, by the respective multiple imaging sequences which are executed in the predetermined order.

It is to be noted that the desired first position indicates a position where a desired first portion of the subject to be examined 1 is placed in the imaging space, and the desired second position indicates a position where a desired second portion of the subject to be examined 1 is placed in the imaging space.

Here, the first portion may be a head region of the subject to be examined 1, and the second portion may be a foot region of the subject to be examined 1.

In addition, the images obtained respectively from the multiple sequences may include images different in contrast.

The images obtained respectively from the multiple sequences may include images different in output morphology.

In the magnetic resonance imaging apparatus of the present embodiment, a moving speed of the table 26, which is controlled by the table controller 27, is set to be equal to or lower than a desired first speed which allows a collection of multiple echo signals being sufficient for reconstructing images as to the regions of the subject to be examined 1 respectively.

In other words, the first speed indicates a speed which satisfies the following: (Travel distance of the table 26 during the time interval for executing one set of multiple sequences in the predetermined order)=(Minimum value of FOV (FOVmin))/(Total phase encoding number (Phase#)/Number of echoes (PN) acquired by one set of multiple sequences executed in the predetermined order).

The sequencer 4 being the imaging control means of the magnetic resonance imaging apparatus according to the present embodiment has control so that the frequency encoding gradient magnetic field is applied in the moving direction of the table 26.

In addition, the magnetic resonance imaging apparatus of the present embodiment further incorporates a living body information detector 28 for acquiring a periodic body motion of the subject to be examined 1, and the sequencer 4 being the imaging control means may be configured in such a manner that the multiple imaging sequences are executed, gated with the body motion period of the subject to be examined 1, which is detected by the living body information detector 28.

In the magnetic resonance imaging apparatus of the present embodiment in which the sequencer 4 being the imaging control means executes the multiple imaging sequences gated with the body motion period of the subject to be examined 1, which is detected by the living body information detector 28, the sequencer 4 being the imaging control means, has control so that all the multiple imaging sequences are executed during at least two periods of the body motion of the subject to be examined 1, which is detected by the living body information detector 28.

In the magnetic resonance imaging apparatus according to the present embodiment in which the sequencer 4 being the imaging control means executes the multiple imaging sequences gated with the body motion period of the subject to be examined 1 detected by the living body information detector 28, it is further possible to configure such that the sequencer 4 being the imaging control means executes multiple imaging sequences so as to obtain images different in morphology during the body motion period of the subject to be examined 1, which is detected by the living body information detector 28.

It is to be noted that the multiple imaging sequences to obtain the images different in morphology may include the cine imaging.

In the magnetic resonance imaging apparatus of the present embodiment in which the sequencer 4, being the imaging control means, executes the multiple imaging sequences gated with the body motion period of the subject to be examined 1, which is detected by the living body information detector 28, the moving speed of the table 26 controlled by the table controller 27 is set to be equal to or lower than a desired second speed which allows a collection of a group of echo signals being sufficient for reconstructing images for the respective regions of the subject to be examined 1.

It is to be noted that the second speed indicates a speed which satisfies the following: (Travel distance of the table 26 during the body motion period)=(Minimum value of FOV)/(Total phase encoding number/Number of echoes acquired during the body motion period×the number of body motion periods required for executing all of one set of imaging sequences).

After execution of the multiple imaging sequences within the predetermined time interval, the table controller 27 of the magnetic resonance imaging apparatus according to the present embodiment, moves the table 26 by a predetermined distance being equal to or lower than the minimum value of FOV in the moving direction of the table 26.

As discussed above, in the present embodiment, an identical encoding amount is applied to each of the multiple imaging sequences and those imaging sequences are executed during a unit cardiac cycle, thereby acquiring echo signals, the number of which is identical in each of the imaging sequences. In addition, the table is moved in the frequency encoding direction gated with the unit cardiac cycle, so that the data items of the respective imaging sequences become continuous in the hybrid space. Therefore, according to the present embodiment, only a single time table movement allows an execution of the multiple imaging sequences gated with the electrocardiogram, and images can be reconstructed according to the results of the multiple imaging sequences, respectively.

In other words, according to the present embodiment, when multiple types of imaging for a wide range are performed while the table is moved, it is possible to reduce an artifact with shortening of total imaging time length. That is, a high quality image can be obtained within a short period of time.

<Fourth Embodiment>

Next, a fourth embodiment will be explained with reference to the accompanying drawings. In each of the embodiments described above, an explanation has been made taking an example that the number of data items in the ky-direction being acquired is the same as to each of the imaging sequences (in the case of cine imaging, as to each of the time phases). However, an imaging sequence with data items the number of which is different in the ky-direction may be mixed. In the present embodiment, an explanation will be made taking an example that includes an imaging sequence for acquiring images being different in spatial resolution. Hereinafter, regarding the present embodiment, only the configuration different from the above embodiments from the first to the third, will be explained.

FIG. 12 illustrates a case where an imaging sequence for acquiring an image having a different spatial resolution is included in the multiple different imaging sequences to be executed. In here, it is assumed that four types of imaging sequences are executed during the unit cardiac cycle.

FIG. 12A shows the measurement space 1001 to 1004 obtained by the respective imaging sequences. Here, the relationship of the number of data items N1, N2, N3, and N4 in the ky-direction, which are acquired by the respective imaging sequences is assumed as N1>N2>N3=N4. On this occasion, in any of the imaging sequences, it is controlled so that all the data items are acquired in the ky-direction in M-times of unit cardiac cycles. In other words, the numbers of echoes for the respective imaging sequences are inputted in such a manner that the number of data items acquired during each unit cardiac cycle becomes N1/M, N2/M, N3/M, and N4/M, respectively. The table travel distance is controlled according to the Formula 3. It is to be noted since (Phase#/PN) represents the unit cardiac cycle, (Phase#/PN)=M is established. Figures from FIG. 12B to FIG. 12D illustrate each state in which the data items obtained by each of imaging sequences are arranged in the hybrid space.

As shown in these figures, even when multiple imaging sequences for acquiring images having different number of data items in the ky-direction are executed, the number of echoes acquired during the unit cardiac cycle is set in such a manner that the number of the unit cardiac cycles becomes the same in each of the imaging sequences, which is necessary for acquiring all the data items in the ky-direction, and the table travel distance is controlled as described above. Accordingly, the data items become continuous in the table moving direction in the hybrid space of each imaging sequence, and therefore, images can be reconstructed respectively from the data items being acquired with a single-time table movement.

<Fifth Embodiment>

Next, a fifth embodiment of the present invention will be explained with reference to the accompanying drawings. In the same manner as the fourth embodiment, an imaging sequence with data items the number of which is different in the ky-direction is mixed. In here, an explanation will be made taking an example that includes an imaging sequence of single-shot type and an imaging sequence of multi-shot type. Hereinafter, as to the present embodiment, only the configuration different from the first to the third embodiments will be explained.

FIG. 13 illustrates an imaging time chart (signal acquisition procedure) including a single-shot type imaging sequence and a multi-shot type imaging sequence (which includes a typical single echo sequence).

As shown in FIG. 13A, the single-shot sequence 1202 and the multi-shot sequence 1204 are executed during the cardiac cycle according to the ECG waveforms 301. It is to be noted that the single-shot sequence 1202 allows an acquisition of all the desired number of echoes during the measurement space 1205-1, but if the multi-shot sequence 1204 requires multiple cardiac cycles to complete all the measurements, the sequences are executed as shown in FIG. 13B, for instance. Here, in the ECG waveforms 301-1 and 301-2, respectively, the single-shot sequence 1207-1 and the multi-shot sequence 1210-1 are executed.

On this occasion, if the single-shot sequence and the multi-shot sequence are executed just by combining in a simple manner, the number of cardiac cycles necessary for acquiring all the data items in the ky-direction becomes different. Therefore, it is controlled as the following for example; the single-shot sequence is subjected to a processing such as setting the number of signals averaged to a larger number, and acquiring data items as to which the direction for applying a diffusion gradient magnetic field is changed, just like a tensor imaging using a diffusion weighted imaging. Such processing brings about a match between the imaging sequences, as to the number of cardiac cycles necessary for acquiring all the data items in the ky-direction. Accordingly, data items being continuous in the table moving direction are acquired in the hybrid space by the respective imaging sequences.

With the control above, it is possible to efficiently execute, gated with living body signals such as heart beats, while the table is moved, both a diffusion weighted imaging throughout the body by using a single-shot echo planar sequence, and an MR angiography imaging throughout the body by using a steady state sequence.

As discussed above, according to each embodiment of the present invention, while moving the table, multiple types of imaging sequences, which are gated with living body signals, can be executed efficiently.

It is to be noted that the embodiments described above are susceptible of various modifications without departing from the scope of the invention. In each the embodiments described above, an explanation has been made, taking an example that a heart beat is utilized as a living body signal that is used as a trigger for the gating. By way of example, it is possible to be gated with a pulse wave or a respiration.

In each of the embodiments above, an explanation has been made taking an example that the table is moved intermittently such as moving the table after the acquisition of data is finished, not moving the table while the data is acquired. However, it is further possible to move the table continuously while the data is collected.

The CPU 8 calculates the table moving speed V in such a manner that the following Formula 4 is satisfied, and the table controller 27 controls the table movement according to the formula:

$$V \leq FOV\text{min}/(TRR \times M \times P) \quad \text{(Formula 4)}$$

Here, "TRR" represents a single cardiac cycle (R-R interval), "M" represents the number of predetermined time intervals required for acquiring echo signals covering the phase encoding direction (ky-direction) entirely in the measuring space, "P" represents the number of unit cardiac cycles, and "FOVmin" represents a minimum value of the FOV size in the frequency encoding gradient magnetic field direction within each of the imaging sequences.

The CPU 8 calculates the position "X" according to the following Formula 5, using an elapsed time t at the point of time when each echo signal is acquired from the time of receiving an ECG waveform, and the table moving speed V.

$$X = V \times t \quad \text{(Formula 5)}$$

Then, a displacement of the acquired echo signal is corrected by using the calculated position X. For example, various methods are employed for the correction, such as a method of shifting the position at the time of image reconstruction, and a method of changing a received frequency at the time of signal measurement.

Furthermore, the imaging sequences for acquiring images different in contrast described above may vary, not only in the repetition time of the imaging sequence and the echo signal acquisition time, but also different in types of sequences themselves, or in conditions such as whether there exists a prepulse or not. It is to be noted in each of the embodiments, imaging of a single slice is described for ease of explanation. However, it is possible to apply the present invention to a multi-slice imaging or a three-dimensional imaging.

The first position and the second position are not necessarily targeted to the head region and the leg region respectively. Those positions may be targeted to a chest region or any of other regions. Furthermore, a periodic body motion of the subject to be examined may be a cardiac cycle, but a respiration cycle is also applicable. In each of the embodiments described above, the imaging sequence is made to be gated with the periodic body motion of the subject to be examined. However, in the case where it is not gated with the periodic body motion of the subject to be examined, it is needless to say that a similar effect can be achieved.

As discussed above, the magnetic resonance imaging apparatus according to the present embodiment incorporates the sequencer 4 being an imaging control means for executing an imaging sequence to image a desired area of a subject to be examined 1, the CPU 8 operating as a signal processing means for reconstructing an image from the signals obtained from a result of executing the imaging sequence, and the table controller 27 for controlling movement of the table 26 on which the subject to be examined is placed. The sequencer 4 being the imaging control means executes multiple imaging sequences while the table controller 27 moves the table 26 from a desired first position to a desired second position with the passage of time, and the CPU 8 being the signal processing means reconstructs images respectively by the multiple sequences as to an area from the first position to the second position, using the signals obtained as a result of executing each of the multiple imaging sequence.

In addition, the sequencer 4 being the imaging control means of the magnetic resonance imaging apparatus in the above case executes the multiple imaging sequences in a predetermined order.

In addition, the sequencer 4 being the imaging control means of the magnetic resonance imaging apparatus in the above case executes the multiple imaging sequences in the predetermined order, thereby acquiring multiple echo signals for obtaining the multiple images.

In the magnetic resonance imaging apparatus in the case above, at least one echo signal is collected for constituting a part of the measurement space for reconstructing the multiple images, by the respective multiple imaging sequences which are executed in the predetermined order.

It is to be noted that the desired first position indicates a position where a desired first portion of the subject to be examined 1 is placed in the imaging space, and the desired second position indicates a position where a desired second portion of the subject to be examined 1 is placed in the imaging space.

Here, the first portion may be a head region of the subject to be examined 1, and the second portion may be a foot region of the subject to be examined 1.

In addition, the images obtained respectively from the multiple sequences may include images different in contrast.

The images obtained respectively from the multiple sequences may include images being different in spatial resolution.

The images obtained respectively from the multiple sequences may include images different in output morphology.

In the magnetic resonance imaging apparatus in the case above, a moving speed of the table 26, which is controlled by the table controller 27, is set to be equal to or lower than a desired first speed which allows a collection of multiple echo signals being sufficient for reconstructing images as to the regions of the subject to be examined 1 respectively.

The sequencer 4 being the imaging control means of the magnetic resonance imaging apparatus in the case above has control so that the frequency encoding gradient magnetic field is applied in the moving direction of the table 26.

In addition, the magnetic resonance imaging apparatus in the case above further incorporates a living body information detector 28 for acquiring a periodic body motion of the subject to be examined 1, and the sequencer 4 being the imaging control means may be configured in such a manner that the multiple imaging sequences are executed, gated with the body motion period of the subject to be examined 1, which is detected by the living body information detector 28.

In the magnetic resonance imaging apparatus in the case above in which the sequencer 4 being the imaging control means executes the multiple imaging sequences gated with the body motion period of the subject to be examined 1, which is detected by the living body information detector 28, the sequencer 4 being the imaging control means, has control so that at least two imaging sequences are executed during a single body motion period of the subject to be examined 1, which is detected by the living body information detector 28.

In the magnetic resonance imaging apparatus in the case above in which the sequencer 4 being the imaging control means, executes the multiple imaging sequences, gated with the body motion period of the subject to be examined 1, which is detected by the living body information detector 28, the moving speed of the table 26 controlled by the table controller 27 is set to be equal to or lower than a desired second speed which allows a collection of a group of echo signals being sufficient for reconstructing images for the respective regions of the subject to be examined 1.

It is to be noted that the second speed indicates a speed which satisfies the following: (Travel distance of the table 26 during the body motion period)=(Minimum value of FOV)/(Total phase encoding number/Number of echoes acquired during the body motion period×Number of body motion periods required for executing all of one set of imaging sequences).

After execution of the multiple imaging sequences within the predetermined time interval, the table controller 27 of the magnetic resonance imaging apparatus in the case above moves the table 26 by a predetermined distance being equal to or lower than the minimum value of FOV, in the table moving direction of the table 26.

In addition, the table control section 27 of the magnetic resonance imaging apparatus in the case above moves the table 26 at a third speed, which is obtained by dividing a distance between the first position and the second position by a time length for acquiring the echo signals the number of which is necessary for reconstructing images in the area from the first position to the second position.

It is to be noted that the multiple imaging sequences in the magnetic resonance imaging apparatus in the case above may include a single-shot type imaging sequence and a multi-shot type imaging sequence.

BRIEF DESCRIPTION OF DRAWINGS

FIG. 4A to 4D illustrate a concept of a typical moving table imaging;

FIG. 7 shows a process flow of the imaging process according to the first embodiment;

FIG. 10 shows a process flow of the imaging process according to the second embodiment;

FIGS. 11A and 11B illustrates a concept of imaging according to the third embodiment;

Denotation of the Reference Numerals

Figure 1:
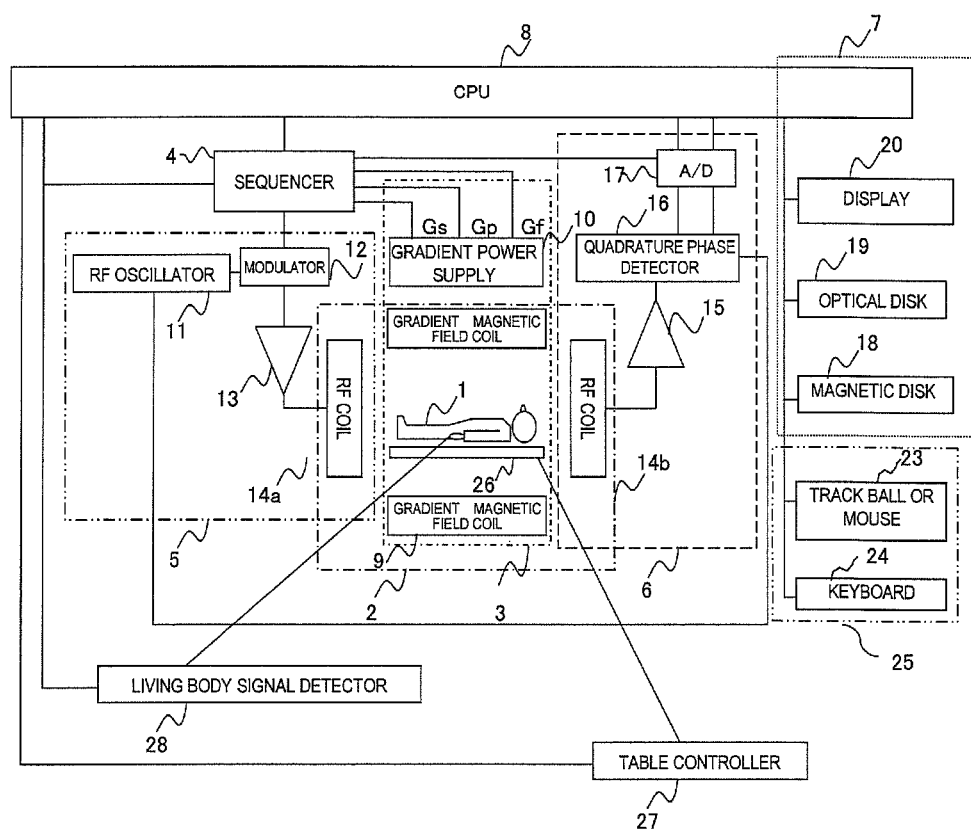
FIG. 1 is an overall configuration diagram of the MRI apparatus according to the first embodiment.
Figure 2A:
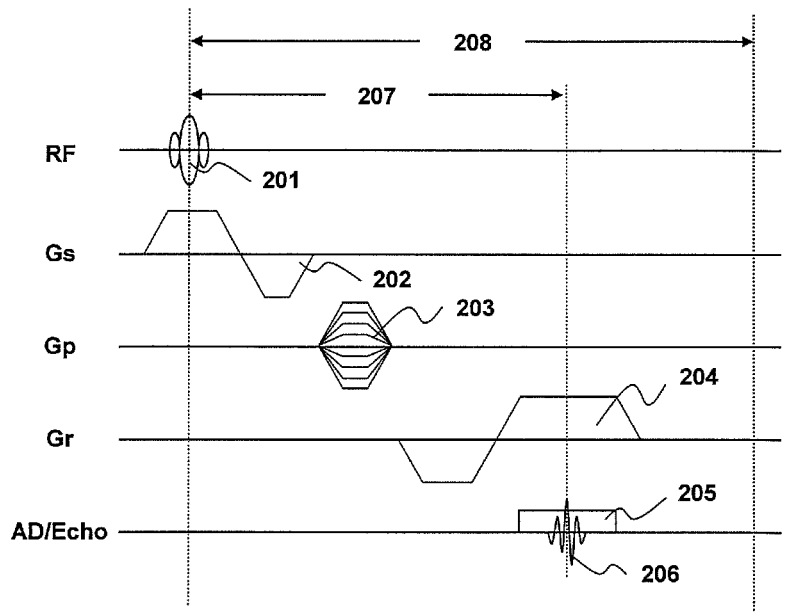
FIG. 2A illustrates an imaging sequence of a typical gradient echo.
Figure 2B:
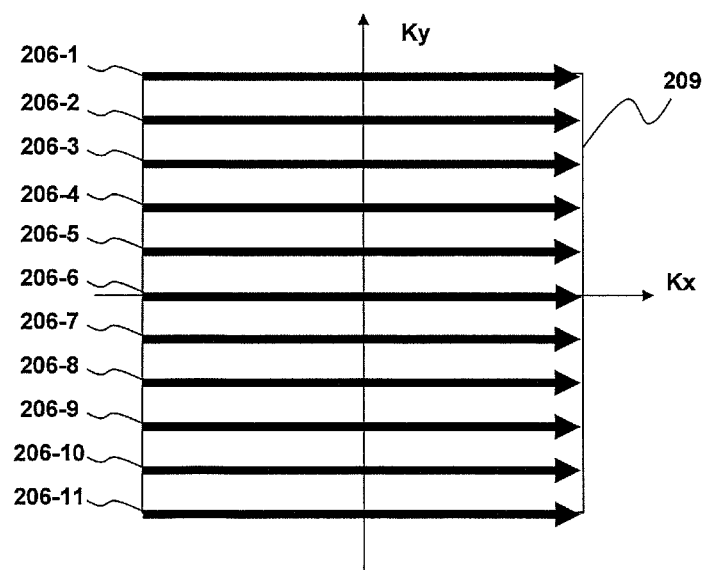
FIG. 2B illustrates a group (at least one echo signal constitutes the group) of echo signals
Figure 3A:
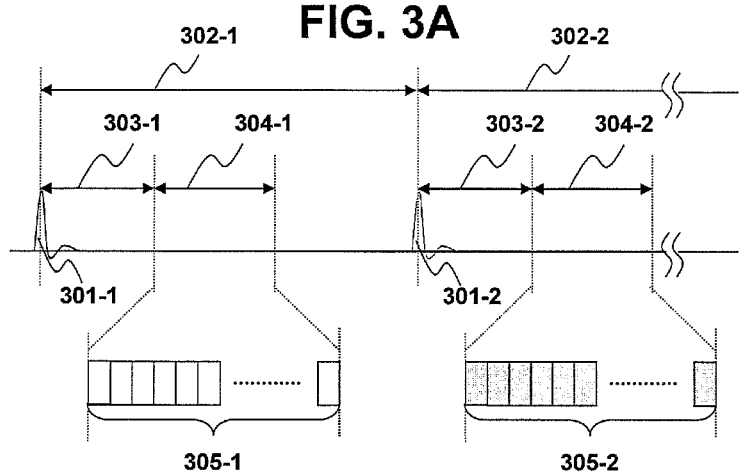
FIG. 3A to FIG. 3D illustrate a concept of a typical gated measurement.
Figure 3B:
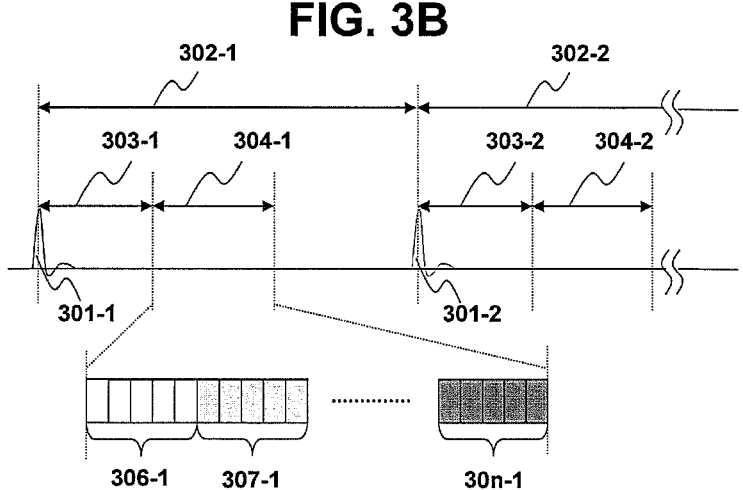
Figure 3C:
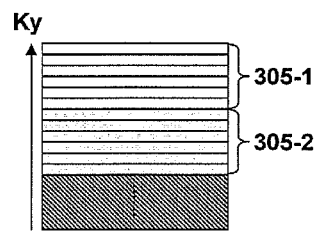
Figure 3D:
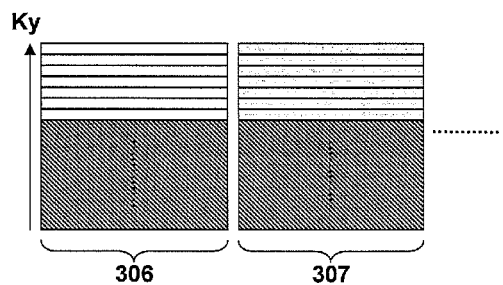
Figure 5:
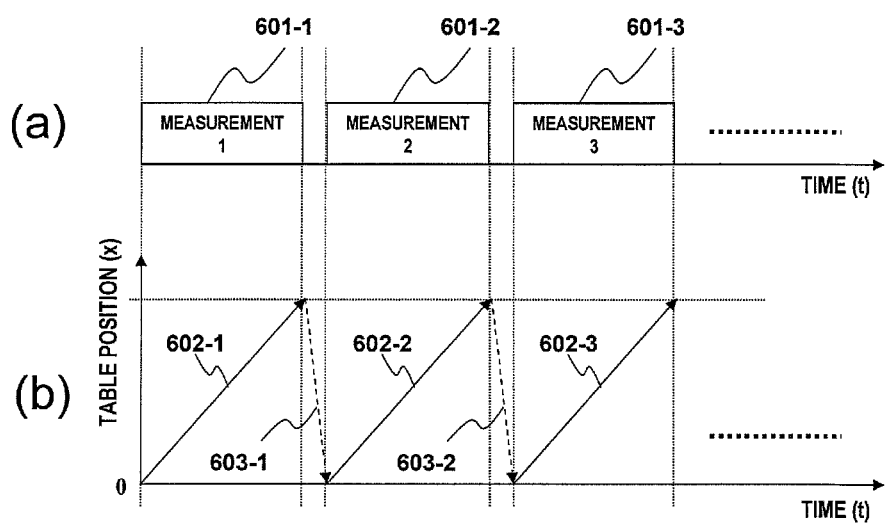
FIG. 5 illustrates an example for executing multiple imaging sequences in the typical moving table imaging.
Figure 6A:
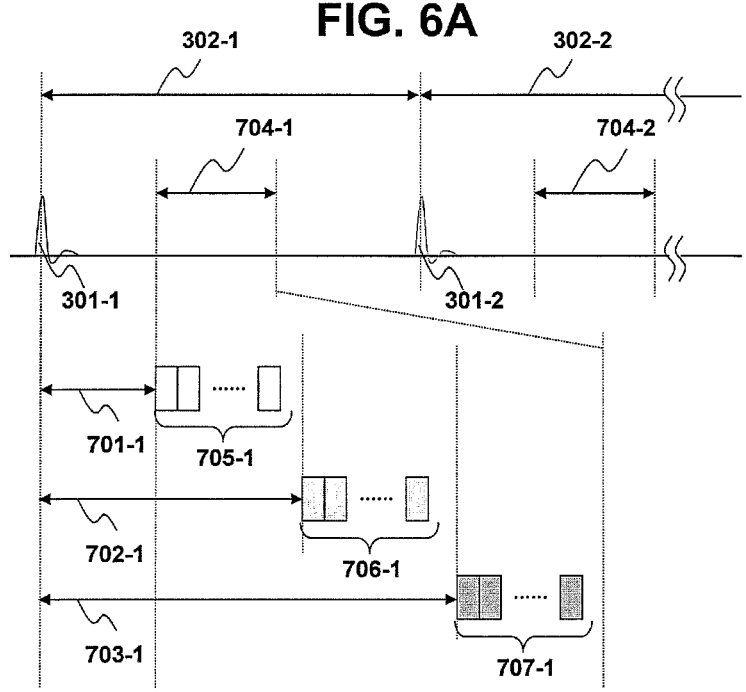
FIG. 6A to 6C illustrates a concept of the imaging according to the first embodiment.
Figure 6B:
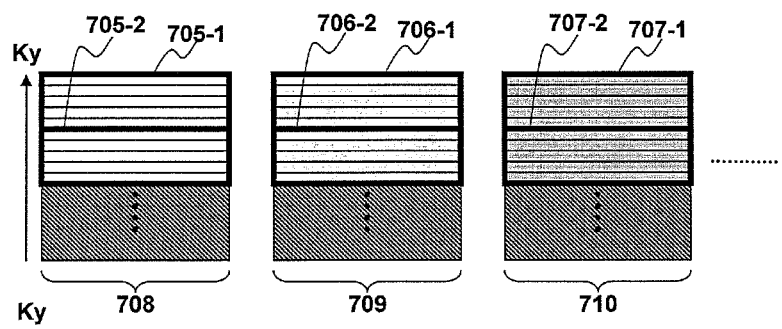
Figure 6C:
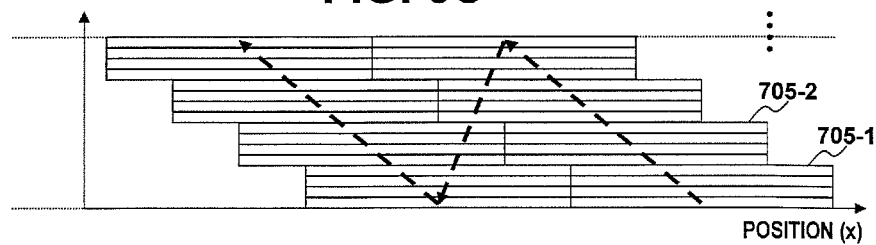
Figure 8:
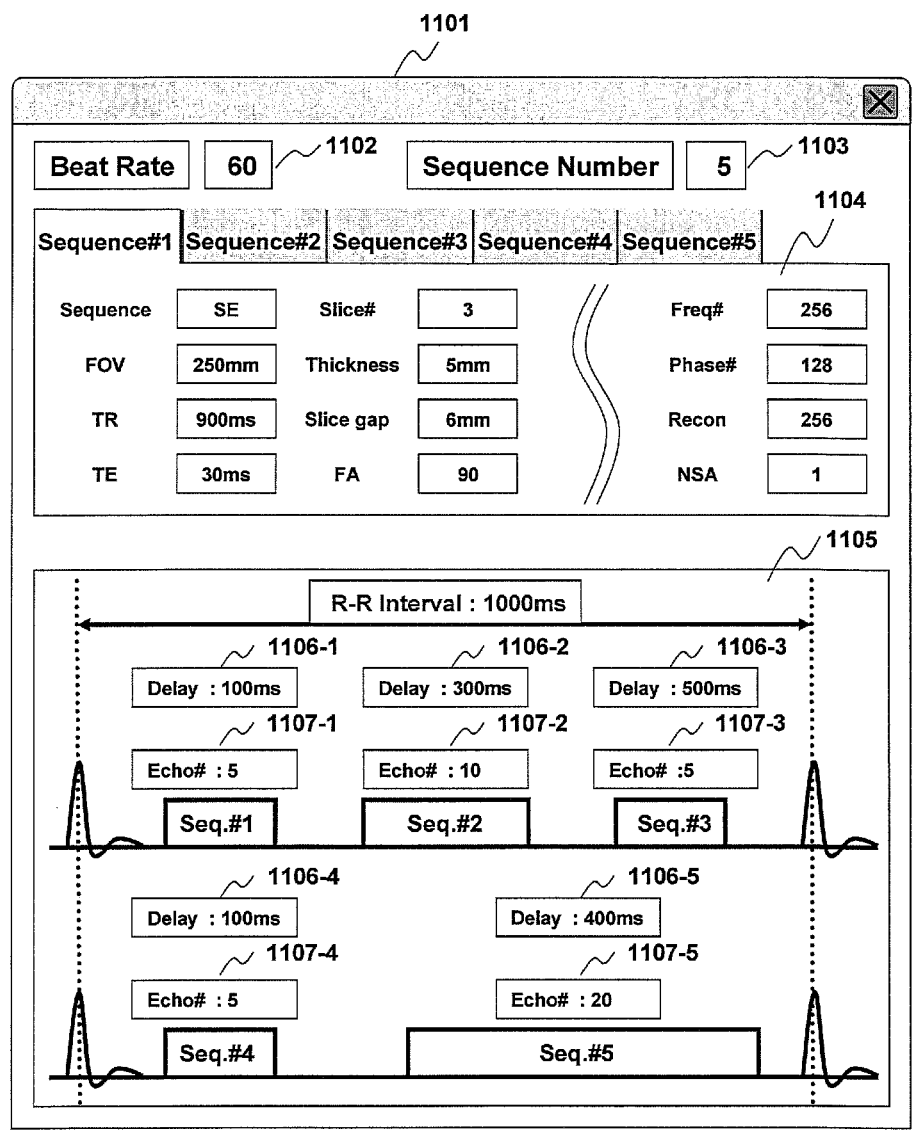
FIG. 8 illustrates an example of input screen according to the first embodiment.
Figure 9A:
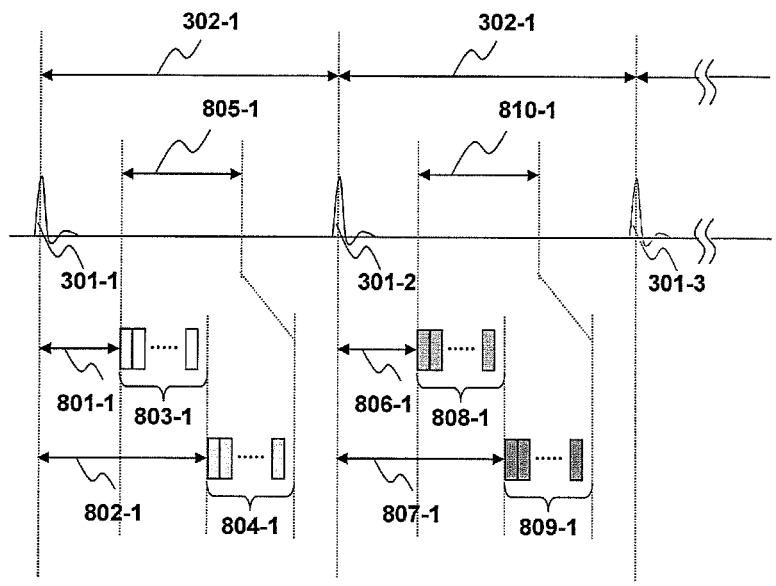
FIGS. 9A and 9B illustrate a concept of imaging according to the second embodiment.
Figure 9B:
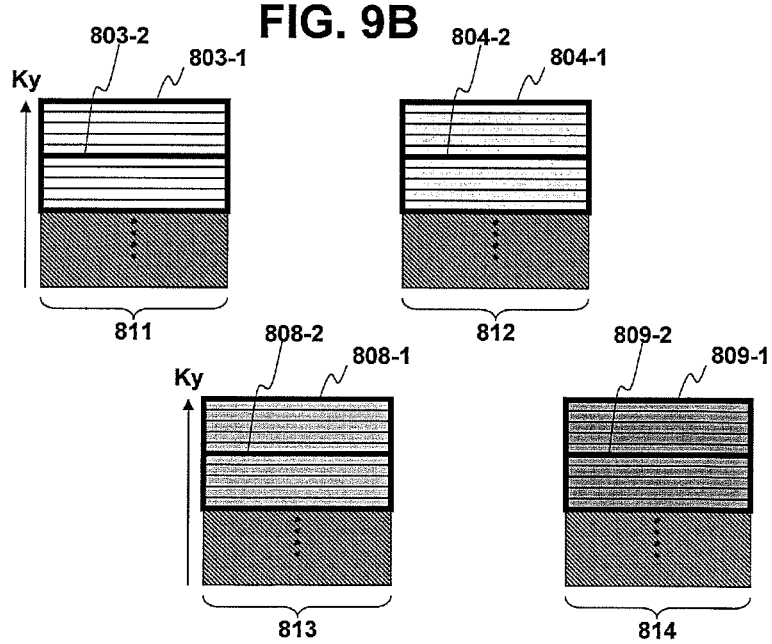
Figure 12A:
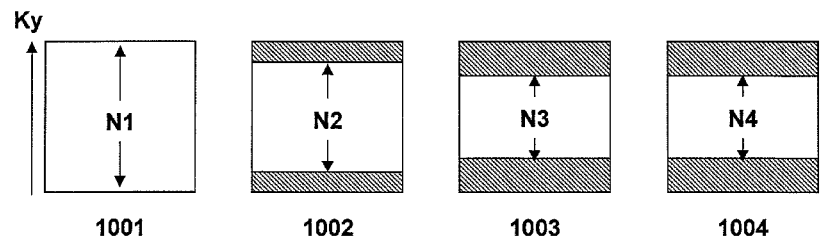
FIG. 12A to 12D illustrate examples where imaging sequences for acquiring images different in spatial resolution are included in each of the embodiments.
Figure 12B:
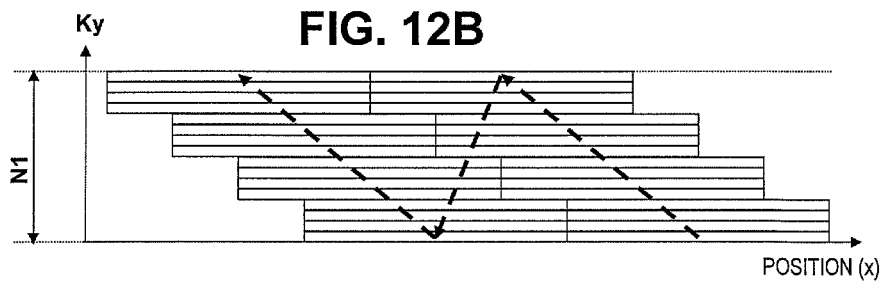
Figure 12C:
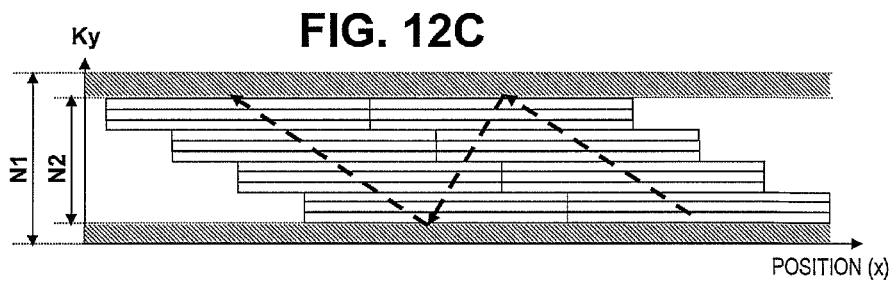
Figure 12D:
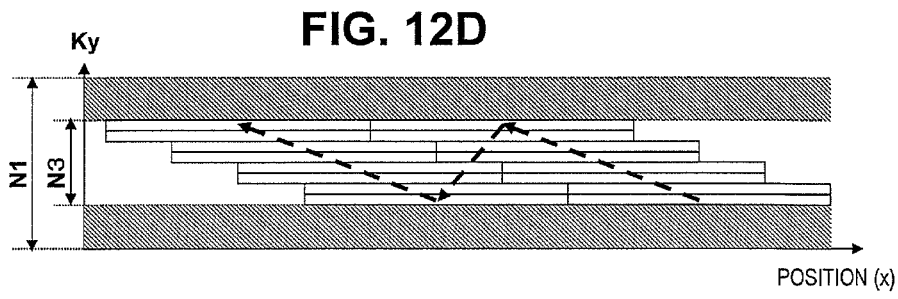
Figure 13A:
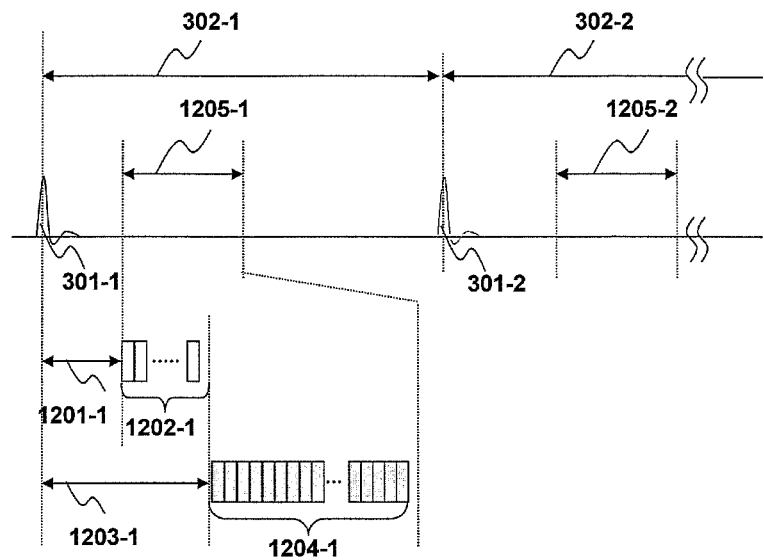
FIGS. 13A and 13B illustrates examples where a single-shot type sequence and a multi-shot type sequence are included in each of the embodiments.
Figure 13B:
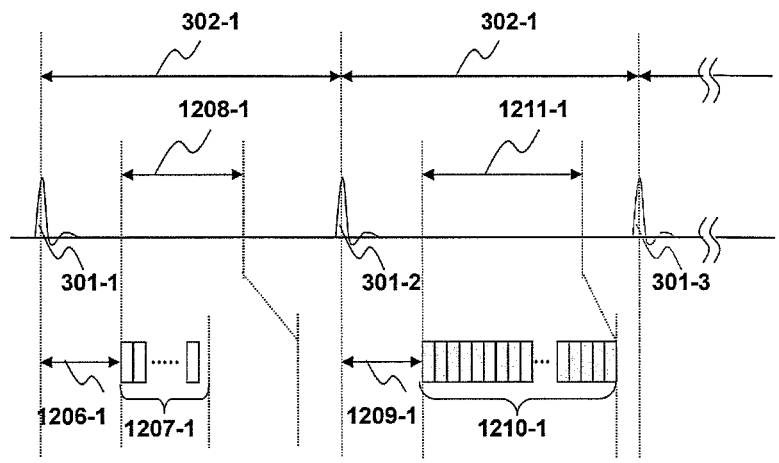

1: SUBJECT TO BE EXAMINED, 2: STATIC MAGNETIC FIELD GENERATION SYSTEM, 3: GRADIENT MAGNETIC FIELD GENERATION SYSTEM, 4: SEQUENCER, 5: SENDING SYSTEM, 6: RECEIVING SYSTEM, 7: SIGNAL PROCESSING SYSTEM, 8: CENTRAL PROCESSING UNIT (CPU), 9: GRADIENT MAGNETIC FIELD COIL, 10: GRADIENT POWER SUPPLY, 11: RF OSCILLATOR, 12: MODULATOR, 13: RF AMPLIFIER, 14a: RF COIL (SENDING SIDE), 14b: RF COIL (RECEIVING SIDE), 15: AMPLIFIER, 16: QUADRATURE PHASE DETECTOR, 17: A/D CONVERTER, 18: MAGNETIC DISK, 19: OPTICAL DISK, 20: DISPLAY, 201: RF PULSE, 202: SLICE SELECTIVE GRADIENT MAGNETIC FIELD, 203: PHASE ENCODING GRADIENT MAGNETIC FIELD, 204: FREQUENCY ENCODING GRADIENT MAGNETIC FIELD, 205: DATA SAMPLING WINDOW, 206: ECHO SIGNAL, 301: ECG WAVEFORM, 302: R-R-INTERVAL, 303: DELAY TIME, 304: MEASUREMENT TIME, 305: IMAGING SEQUENCE, 306: IMAGING SEQUENCE, 307: IMAGING SEQUENCE, 701: DELAY TIME, 702: DELAY TIME, 703: DELAY TIME, 704: MEASUREMENT TIME, 705: IMAGING SEQUENCE, 706: IMAGING SEQUENCE, 707: IMAGING SEQUENCE

What is claimed is:

1. A magnetic resonance imaging apparatus comprising a sequencer unit that executes an imaging sequence to image a desired area of a subject to be examined;
a processing unit configured by one or more computer programs to reconstruct an image from signals obtained from a result of executing the imaging sequence;
a table controller unit that controls movement of a table on which the subject to be examined is placed; and
a living body signal detector unit that acquires a body motion period of the subject to be examined, wherein
the sequencer unit executes multiple imaging sequences while the table controller unit moves the table from a desired first position to a desired second position with the passage of time, in one direction, gated with the body motion period of the subject to be examined, detected by the living body signal detector unit, and
the sequencer unit collects echo signals for reconstructing multiple images over multiple body motion periods of the subject, including, for each specific k-space measurement space of multiple measurement spaces to be filled by each of the multiple imaging sequences respectively over the multiple body motion periods of the subject, collecting at least one echo signal for a portion of the specific measurement space over at least one body motion period of the subject, and collecting an echo signal for another portion of the specific measurement space over another body motion period of the subject, and
the processing unit reconstructs multiple images corresponding to the multiple sequences as to a targetted area from the first position to the second position, using the echo signals obtained as a result of executing each of the multiple imaging sequences over the same targetted area from the first position to the second position.

2. The magnetic resonance imaging apparatus according to claim wherein,
the sequencer unit executes the multiple imaging sequences in a predetermined order.

3. The magnetic resonance imaging apparatus according to claim 2, wherein the sequencer unit executes the multiple imaging sequences in the predetermined order o as to acquire multiple echo signals for the processing unit to reconstruct the multiple images.

4. The magnetic resonance imaging apparatus according to claim 3, wherein,
a moving speed of the table which is controlled by the table controller unit, is set to be equal to or lower than a desired first speed which allows a collection of multiple echo signals being sufficient for reconstructing images as to the regions of the subject to be examined respectively.

5. The magnetic resonance imaging apparatus according to claim 4, wherein the desired first speed indicates a speed which satisfies the following:

(Travel distance of the table at the desired first speed during a time interval for executing one set of multiple sequences in the predetermined order) =(Minimum value of $FOV$)/ (Total phase encoding number/Number of echoes acquired by one set of multiple sequences executed in the predetermined order).

6. The magnetic resonance imaging apparatus according to claim 1, wherein,
the desired first position indicates a position where a desired first portion of the subject to be examined is placed within imaging space, and the desired second position indicates a position where a desired second portion of the subject to be examined is placed within the imaging space.

7. The magnetic resonance imaging apparatus according to claim 6, wherein,
the first portion is a head region of the subject to be examined, and the second portion is a foot region of the subject to be examined.

8. The magnetic resonance imaging apparatus according to claim 1, wherein the multiple images obtained respectively by the multiple sequences include images different in contrast.

9. The magnetic resonance imaging apparatus according to claim 1, wherein the multiple images obtained respectively by the multiple sequences include images different in spatial resolution.

10. The magnetic resonance imaging apparatus according to claim 1, wherein the multiple images obtained respectively by the multiple sequences include images different in output morphology.

11. The magnetic resonance imaging apparatus according to claim 1, wherein,
the sequencer unit applies a frequency encoding gradient magnetic field in a table moving direction.

12. The magnetic resonance imaging apparatus according to claim 1, wherein,
the sequencer unit executes at least two imaging sequences during a single body motion period of the subject to be examined, being detected by the living body signal detector unit.

13. The magnetic resonance imaging apparatus according to claim 1, wherein,
the sequencer unit executes all the multiple imaging sequences during a single body motion period of the subject to be examined, being detected by the living body signal detector unit.

14. The magnetic resonance imaging apparatus according to claim 13, wherein a moving speed of the table which is controlled by the table controller unit is equal to or lower than a particular speed, and the particular speed indicates a speed which satisfies the following:

(Travel distance of the table during the body motion period) =(Minimum value of FOV)/ (Total phase encoding number/Number of echoes acquired during at least two body motion periods).

15. The magnetic resonance imaging apparatus according to claim 1, wherein,
the sequencer unit executes all the multiple imaging sequences during a single body motion period of the subject to be examined, being detected by the living body signal detector unit.

16. The magnetic resonance imaging apparatus according to claim 15, wherein a moving speed of the table which is controlled by the table controller unit is equal to or lower than a particular speed, and the particular speed indicates a speed which satisfies the following:

(Travel distance of the table during the body motion period) =(Minimum value of FOV)/ (Total phase encoding number/Number of echoes acquired during at least two body motion periods).

17. The magnetic resonance imaging apparatus according to claim 1, wherein,
the sequencer unit executes all the multiple imaging sequences during a single body motion period of the subject to be examined, being detected by the living body signal detector unit.

18. The magnetic resonance imaging apparatus according to claim 17, wherein,
the imaging sequences to obtain the images different in morphology are imaging sequences of cine imaging.

19. The magnetic resonance imaging apparatus according to claim 1, wherein a moving speed of the table which is controlled by the table controller unit is set to be equal to or lower than a desired speed which allows a collection of a group of echo signals being sufficient for reconstructing images for the respective regions of the subject to be examined.

20. The magnetic resonance imaging apparatus according to claim 1, wherein after execution of the multiple imaging sequences within a predetermined time interval, the table controller unit moves the table, by a predetermined distance being equal to or lower than the minimum value of FOV in the table moving direction.

21. The magnetic resonance imaging apparatus according to claim 1, wherein the table controller unit moves the table continuously at a speed equal to or lower than a specific speed, and the specific speed indicates a speed which satisfies the following:

specific speed=(Distance between the first position and the second position)/ (Number of echo signals which is necessary for reconstructing images in the area from the first position to the second position)×(Time interval for acquiring each of the echo signals).

22. The magnetic resonance imaging apparatus according to claim 1, wherein,
the multiple imaging sequences include a single-shot type imaging sequence and a multi-shot type imaging sequence.

23. A magnetic resonance imaging method using a magnetic resonance imaging apparatus for executing multiple imaging sequences to image a desired area of a subject to be examined, while moving a table on which the subject to be examined is placed, and for reconstructing images from echo signals obtained from the multiple imaging sequences, comprising:
(a) acquiring a body motion period of the subject to be examined;
(b) executing the multiple imaging sequences while the table moves from a desired first position to a desired second position with the passage of time, in one direction, gated with the body motion period of the subject to be examined, and collecting echo signals for reconstructing multiple images over multiple body motion periods of the subject, including, for each specific k-space measurement space of multiple measurement spaces to be filled by each of the multiple imaging sequences respectively over the multiple body motion periods of the subject, collecting at least one echo signal for a portion of the specific measurement space over at least one body motion period of the subject, and collecting an echo signal for another portion of the specific measurement space over another body motion period of the subject; and
c) reconstructing multiple images corresponding to the multiple sequences as to a targetted area from the first position to the second position, using the echo signals obtained as a result of executing each of the multiple imaging sequences over the same targetted area from the first position to the second position.

24. The magnetic resonance imaging method according to claim 23, further comprising:
(b1) accepting from an operator, an input of imaging parameters respectively for the multiple imaging sequences; and (b2) repeating the following:
    executing the multiple imaging sequences according to the imaging parameters accepted in (b1), within a predetermined time interval in a predetermined order, so as to perform a measurement to receive a predetermined number of echo signals from each of the imaging sequences; and after the measurement, moving the table by a predetermined distance prior to the next time interval, thereby acquiring all the echo signals as to the area from the first position to the second position.

\* \* \* \* \*